(12) United States Patent
Ohigashi

(10) Patent No.: US 8,952,137 B2
(45) Date of Patent: *Feb. 10, 2015

(54) METHOD FOR PRODUCING HIGH-PURITY SOLUBLE THROMBOMODULIN

(75) Inventor: Susumu Ohigashi, Shiga (JP)

(73) Assignee: Asahi Kasei Pharma Corporation, Tokyo (JP)

(*) Notice: Subject to any disclaimer, the term of this patent is extended or adjusted under 35 U.S.C. 154(b) by 135 days.

This patent is subject to a terminal disclaimer.

(21) Appl. No.: 13/557,645

(22) Filed: Jul. 25, 2012

(65) Prior Publication Data

US 2013/0237693 A1    Sep. 12, 2013

Related U.S. Application Data

(62) Division of application No. 12/532,598, filed as application No. PCT/JP2008/055211 on Mar. 21, 2008, now Pat. No. 8,258,269.

(30) Foreign Application Priority Data

Mar. 23, 2007  (JP) ................. 2007-077389

(51) Int. Cl.
| | | |
|---|---|---|
| A23J 1/00 | (2006.01) | |
| C07K 1/18 | (2006.01) | |
| C07K 14/745 | (2006.01) | |
| C07K 1/16 | (2006.01) | |

(52) U.S. Cl.
CPC ............... *C07K 1/18* (2013.01); *C07K 14/7455* (2013.01); *C07K 1/165* (2013.01)
USPC .......................................... 530/412; 530/416

(58) Field of Classification Search
None
See application file for complete search history.

(56) References Cited

U.S. PATENT DOCUMENTS

| | | | |
|---|---|---|---|
| 5,043,425 A | 8/1991 | Aoki et al. | |
| 5,202,421 A | 4/1993 | Kunihiro et al. | |
| 5,300,490 A | 4/1994 | Kunihiro et al. | |
| 5,466,668 A | 11/1995 | Glaser et al. | |
| 5,516,659 A | 5/1996 | Nii et al. | |
| 5,574,007 A | 11/1996 | Zushi et al. | |
| 5,695,964 A | 12/1997 | Nii et al. | |
| 5,753,123 A | 5/1998 | Kajihara et al. | |
| 5,827,824 A | 10/1998 | Light et al. | |
| 5,834,028 A | 11/1998 | Kunihiro et al. | |
| 6,034,060 A | 3/2000 | Yamamoto et al. | |
| 6,063,763 A | 5/2000 | Light et al. | |
| 6,808,706 B1 | 10/2004 | Yui et al. | |
| 2002/0010319 A1 | 1/2002 | Ansaldi et al. | |
| 2004/0116674 A1 | 6/2004 | Ansaldi et al. | |
| 2006/0083733 A1 | 4/2006 | Nishio | |

FOREIGN PATENT DOCUMENTS

| | | |
|---|---|---|
| EP | 0376251 A2 | 7/1990 |
| EP | 0412841 A1 | 2/1991 |
| EP | 0445681 A2 | 9/1991 |
| EP | 0474273 A2 | 3/1992 |
| EP | 0356836 B1 | 5/1994 |
| EP | 1 475 098 A1 | 11/2004 |
| JP | 64-6219 A | 1/1989 |
| JP | 2-255699 A | 10/1990 |
| JP | 3-86900 A | 4/1991 |
| JP | 3-133380 A | 6/1991 |
| JP | 3-218399 A | 9/1991 |
| JP | 3-259084 A | 11/1991 |
| JP | 4-210700 A | 7/1992 |
| JP | 5-213998 A | 8/1993 |
| JP | 6-321805 A | 11/1994 |
| JP | 7-173189 A | 7/1995 |
| JP | 9-110900 A | 4/1997 |
| JP | 11-171790 A | 6/1999 |
| JP | 11-341990 A | 12/1999 |
| JP | 3007785 B2 | 2/2000 |
| TW | 408129 B | 10/2000 |
| WO | WO 92/00325 A1 | 1/1992 |
| WO | WO 92/03149 A1 | 3/1992 |
| WO | 93/15755 A1 | 8/1993 |
| WO | 95/16460 A1 | 6/1995 |

(Continued)

OTHER PUBLICATIONS

Bates, Shannon, et al., "New anticoagulants: beyond heparin, low-molecular-weight heparin and warfarin," British Journal of Pharmacology, vol. 144, No. 8, pp. 1017-1028, Feb. 14, 2005.

(Continued)

*Primary Examiner* — Suzanne M Noakes
*Assistant Examiner* — Jae W Lee
(74) *Attorney, Agent, or Firm* — Birch, Stewart, Kolasch & Birch, LLP

(57) ABSTRACT

A method is provided for producing soluble thrombomodulin substantially not containing a denatured product of the soluble thrombomodulin that is generated under acidic conditions, which comprises: subjecting the soluble thrombomodulin-containing material to an anion exchanger or hydroxyapatite; and carrying out linear gradient elution, stepwise gradient elution, or gradient elution in which linear gradient elution is combined with stepwise gradient elution under separation conditions in which the denatured product of the soluble thrombomodulin can be separated, wherein the gradient is a salt concentration gradient, so as to obtain an elution fraction containing soluble thrombomodulin that does not substantially contain the denatured product of the soluble thrombomodulin, either (a) after the position of a fraction has previously been confirmed, or (b) while confirming the elution fraction.

17 Claims, 4 Drawing Sheets

(56) References Cited

FOREIGN PATENT DOCUMENTS

| WO | 99/18994 A1 | 4/1999 |
|---|---|---|
| WO | 99/62936 A1 | 12/1999 |
| WO | 03/061687 A1 | 7/2003 |

OTHER PUBLICATIONS

Bourin et al., "Functional domains of rabbit thrombomodulin", Proc. Natl. Acad. Sci., vol. 83, pp. 5924-5928, Aug. 1986.
Decision dated Oct. 20, 2011, issued in corresponding Taiwanese Patent Application No. 097110165.
Examination report dated Apr. 28, 2011, issued in corresponding Canadian Patent Application No. 2,681,294.
Examination Report dated Apr. 28, 2011, issued in corresponding New Zealand Patent Application No. 579873.
Examination Report dated Feb. 2, 2012, issued in corresponding Singapore Patent Application No. 2009060963.
Examination Report dated Oct. 1, 2010, issued in corresponding New Zealand Patent Application No. 579873.
Examiner's Report dated Jun. 15, 2011, issued in corresponding Australian Patent Application No. 2008230465.
Examiner's report dated Sep. 17, 2010, issued in corresponding Australian Patent Application No. 2008230465.
Gomi, Komakazy, et al., "Antithrombotic Effect of Recombinant Human Thrombomodulin on Thrombin-Induced Thromboembolism in Mice," Blood, vol. 75, No. 7, pp. 1396-1399, Apr. 1, 1990.
International Search Report dated May 13, 2008 in Application No. PCT/JP2008/055211 in English.
Korean Office Action dated Mar. 31, 2012 issued in Korean patent application No. 10-2009-7017230.
Office Action dated Apr. 29, 2011, issued in Korean Patent Application No. 10-2009-7017230.
Office Action dated Feb. 21, 2011, issued in corresponding Taiwanese Patent Application No. 097110165.
Office Action dated Feb. 28, 2011, issued in corresponding Japanese Patent Application No. 2009-506314.
Office Action dated Jul. 10, 2012, issued in corresponding Japanese Patent Application No. 2009-506314.
Office Action dated Jun. 4, 2012, issued in corresponding Canadian Application No. 2,681,294.
Office Action dated Oct. 26, 2011, issued in corresponding Chinese Patent Application No. 200880009625.7.
Office Action dated Oct. 27, 2011, issued in corresponding European Patent Application No. 08722575.1.
The extended European Search Report issued in European Patent Application No. 08722575.1 on Jan. 12, 2011.
Watanabe, Yasushi et al., "Assessment Study on the High-Performance Liquid Chromatography-Type Hydroxyapatite Chromatography in the Presence of Sodium Dodecyl Sulfate," Analytical Biochemistry, vol. 202, pp. 268-274, 1992.
Wen, Daunzhi, et al., "Human Thrombomodulin: Complete cDNA Sequence and Chromosome Localization of the Gene," Biochemistry, vol. 26. No. 14, pp. 4350-4357, Jul. 1, 1987.
Written Opinion dated Jun. 13, 2011, issued in corresponding Singapore Patent Application No. 2009060963.
Written Opinion dated Oct. 20, 2010, issued in corresponding Singapore Patent Application No. 2009060963.
Zushi, Michitaka, et al., "The Last Three Consecutive Epidermal Growth Factor-like Structures of Human Thrombomodulin Comprise the Minimum Functional Domain for Protein C-activating Cofactor . . . ," The Journal of Biological Chenistry, vol. 264, No. 18, pp. 10351-10353, Jun. 25, 1989.
Office Action dated Oct. 29, 2012, issued in corresponding European Patent Application No. 08722575.1-1212.
Taiwanese Office Action cited in Taiwanese Patent Application No. 097110165 on Oct. 31, 2013.
Chinese Office Action for Application No. 200880009625.7 dated Sep. 7, 2012 (with English translation).
Canadian Office Action, dated Mar. 26, 2013, for Canadian Application No. 2,681,294.

METHOD FOR PRODUCING HIGH-PURITY SOLUBLE THROMBOMODULIN

CROSS REFERENCE

This application is a Divisional of application Ser. No. 12/532,598 filed on Nov. 6, 2009 now U.S. Pat. No. 8,258,269, and for which priority is claimed under 35 U.S.C. §120. Application Ser. No. 12/532,598 is the national phase of PCT International Application No. PCT/JP2008/055211 filed on Mar. 21, 2008 under 35 U.S.C. §371. Priority is also claimed to JP2007-077389 filed on Mar. 23, 2007. The entire contents of each of the above-identified applications are hereby incorporated by reference.

TECHNICAL FIELD

The present invention relates to a method for producing a high-purity soluble thrombomodulin substantially not containing a denatured product of soluble thrombomodulin that may be generated under acidic conditions.

BACKGROUND ART

Thrombomodulin has been known as a substance that acts to specifically bind to thrombin so as to inhibit the blood coagulation activity thereof, and at the same time, acts to significantly promote the ability of the thrombin to activate protein C. Thrombomodulin has also been known to have strong blood coagulation-inhibiting action. It has also been known that thrombomodulin extends the coagulation time by thrombin, or that it suppresses platelet aggregation due to thrombin. Protein C is a vitamin K-dependent protein that plays an important role in a blood coagulation fibrinolytic system. Protein C is activated by the action of thrombin, so that it becomes activated protein C. It has been known that the activated protein C inactivates an activated blood coagulation factor V and an activated blood coagulation factor VIII in vivo, and that it is involved in generation of a plasminogen activator having thrombolytic action (Non-Patent Document 1). Accordingly, it has been considered that thrombomodulin promotes the activation of protein C by thrombin, and thus that this is useful as an anticoagulant or a thrombolytic agent. Also, it has been reported in an animal experiment that thrombomodulin is effective for therapy or prevention of diseases associated with acceleration of coagulation (Non-Patent Document 2).

Conventionally, thrombomodulin has been discovered and obtained as a glycoprotein that is expressed on the vascular endothelial cells of various animal species, including humans as typical examples, and thereafter has been successfully cloned. That is to say, a human thrombomodulin precursor gene containing a signal peptide has been cloned from a human lung cDNA library by genetic engineering, and all the gene sequences of thrombomodulin have been analyzed. As a result, an amino acid sequence consisting of 575 residues containing a signal peptide (in general, 18 amino acid residues are exemplified) has been clarified (Patent Document 1). It has been known that a mature thrombomodulin, from which the signal peptide has been cleaved, is composed of 5 regions, namely, an N-terminal region (amino acids 1-226: this is the position determined when the signal peptide is assumed to consist of 18 amino acid residues, and the same holds true for other regions), a region having six EGF-like structures (amino acids 227-462), an O-linked glycosylation region (amino acids 463-498), a transmembrane region (amino acids 499-521), and an intracytoplasmic region (amino acids 522-557), from the N-terminal side of the mature peptide. It has also been known that, among the six EGF-like structures, the $4^{th}$, $5^{th}$, and $6^{th}$ EGF-like structure portions from the N-terminal side (that is, minimal units of activity) mainly have the same activity as that of the entire-length thrombomodulin (Non-Patent Document 3).

Unless a surfactant is present, the entire-length thrombomodulin is hardly dissolved. Thus, addition of a surfactant is necessary for producing a thrombomodulin preparation. In contrast, there is also a soluble thrombomodulin that can be fully dissolved even in the absence of a surfactant. The soluble thrombomodulin may be prepared by removing at least a part of the transmembrane region or the entire transmembrane region. For example, it has been confirmed that a soluble thrombomodulin consisting of only 3 regions, namely, an N-terminal region, a region having six EGF-like structures, and an O-linked glycosylation region (that is, a soluble thrombomodulin having an amino acid sequence consisting of amino acids 19-516 of SEQ ID NO: 1), can be obtained by applying recombination techniques, and that this recombinant soluble thrombomodulin has the same activity as that of a native thrombomodulin (Patent Document 1). In addition, there are some other reports regarding soluble thrombomodulins (Patent Documents 2 to 9). Also, a human urine-derived soluble thrombomodulin and the like have been exemplified as native thrombomodulins (Patent Documents 10 and 11).

As recognized in many cases, as a result of spontaneous mutations or mutations occurring when thrombomodulins are obtained, polymorphic mutations have been found even in human genes. At present, thrombomodulin genes in which the amino acid at position 473 of a human thrombomodulin precursor having the aforementioned amino acid sequence consisting of 575 amino acid residues is converted to Val or Ala have been identified. In a nucleotide sequence encoding this amino acid, the nucleotide at position 1418 is converted to T or C (Non-Patent Document 4). However, the two thrombomodulins are completely identical in terms of their activity and physical properties. Thus, it can be considered that they are substantially identical.

It has been reported that thrombomodulin has effects on the therapy of DIC (Non-Patent Document 5). In addition to the aforementioned intended uses, it is anticipated that thrombomodulin will be used in the therapy and prevention of various diseases such as acute coronary syndrome (ACS), thrombosis, peripheral vascular obstruction, arteriosclerosis obliterans, vasculitis, functional disorder occurring after heart surgery, complication caused by organ transplantation, angina pectoris, transient ischemic attack, toxemia of pregnancy, diabetes, liver VOD (liver veno-occlusive disease; e.g. fulminant hepatitis, veno occlusive disease of liver occurring after bone marrow transplantation), deep venous thrombosis (DVT), and adult respiratory distress syndrome (ARDS).

As denatured products of thrombomodulin, an aggregate generated in a freeze-drying process and an aggregate generated during long-term preservation in a freeze-dried state have been known (Patent Documents 12 to 16).

Known methods for producing soluble thrombomodulin at an industrial level for use in pharmaceutical products include: a method using affinity chromatography in which an antibody reacting with thrombomodulin is supported in a purification step; a method for producing high-purity soluble thrombomodulin substantially containing neither serum-derived products nor antibody-derived products, which is characterized in that the soluble thrombomodulin is obtained as a pass-through fraction in a step of allowing the soluble thrombomodulin obtained by affinity chromatography to come into contact with a cation exchanger under conditions consisting of a specific conductivity of 25 to 34 ms/cm and pH 3 to 4 (Patent Document 17); and a method for purifying thrombomodulin, which is characterized in that it comprises preliminarily purifying a human urine thrombomodulin-containing sample by thrombin-bound affinity chromatography and then purifying the sample by adsorption chromatography using hydroxyapatite as an adsorbent (Patent Document 18).

Patent Document 1: JP Patent Publication (Kokai) No. 64-6219 A (1989)
Patent Document 2: JP Patent Publication (Kokai) No. 2-255699 A (1990)
Patent Document 3: JP Patent Publication (Kokai) No. 3-133380 A (1991)
Patent Document 4: JP Patent Publication (Kokai) No. 3-259084 A (1991)
Patent Document 5: JP Patent Publication (Kokai) No. 4-210700 A (1992)
Patent Document 6: JP Patent Publication (Kokai) No. 5-213998 A (1993)
Patent Document 7: WO92/00325
Patent Document 8: WO92/03149
Patent Document 9: WO93/15755
Patent Document 10: JP Patent Publication (Kokai) No. 3-86900 A (1991)
Patent Document 11: JP Patent Publication (Kokai) No. 3-218399 A (1991)
Patent Document 12: JP Patent Publication (Kokai) No. 6-321805 A (1994)
Patent Document 13: JP Patent No. 3007785
Patent Document 14: JP Patent Publication (Kokai) No. 11-171790 A (1999)
Patent Document 15: WO95/16460
Patent Document 16: JP Patent No. 3822383
Patent Document 17: JP Patent Publication (Kokai) No. 11-341990 A (1999)
Patent Document 18: JP Patent No. 3745805
Non-Patent Document 1: Koji Suzuki, *Igaku no Ayumi* (Progression of Medicines), Vol. 125, p. 901 (1983)
Non-Patent Document 2: K. Gomi et al., Blood 75, 1396-1399 (1990)
Non-Patent Document 3: M. Zushi et al., J. Biol. Chem., 264, 10351-10353 (1989)
Non-Patent Document 4: D. Z. Wen et al., Biochemistry, 26, 4350-4357 (1987)
Non-Patent Document 5: S. M. Bates et al., Br. J. of Pharmacol., 144, 1017-1028 (2005)

DISCLOSURE OF THE INVENTION

Object to be Solved by the Invention

It is an object of the present invention to provide a method for producing thrombomodulin substantially not containing a denatured product of soluble thrombomodulin with high productivity.

Means for Solving the Object

In a process of producing soluble thrombomodulin at an industrial level, or in a method for producing soluble thrombomodulin comprising a step of inactivating viruses under acidic conditions, the present inventor has found a novel object that a denatured product of soluble thrombomodulin is generated when the soluble thrombomodulin is left under acidic conditions and the denatured product of soluble thrombomodulin should be efficiently eliminated. In order to eliminate the denatured product of the soluble thrombomodulin, the present inventor has studied the use of gel filtration chromatography (GFC), size exclusion chromatography (SEC), and the like. However, the present inventor has found that the gel filtration chromatography (GFC) or the size exclusion chromatography (SEC) has small processing capacity, and thus that its column volume should be increased (common column volume: 5% or less) or multiple cycles are necessary. In addition, as a method of increasing efficiency, an increase in the linear velocity of chromatography is considered. However, such increase in the linear velocity is not appropriate because it decreases separation capacity. Moreover, as another method, an increase in the concentration of the processed protein is also considered. However, this method is problematic in terms of an addition of a concentration step for increasing the protein concentration, a decrease in separation capacity caused by high viscosity due to a high protein concentration, and the like.

Thus, in order to produce soluble thrombomodulin at an industrial level to be directed towards achieving the aforementioned object of the present invention, the present inventor has considered it important to separate a denatured product of the soluble thrombomodulin by a method involving high productivity, by which the aforementioned object has been achieved. In order to achieve the aforementioned novel object, the present inventor has conducted intensive studies regarding various conditions using various chromatographic carriers. As a result, the present inventor has succeeded in finding a method for efficiently and stably separating a denatured product of the soluble thrombomodulin by using an anion exchanger or hydroxyapatite as a carrier and by determining conditions suitable for each of the carriers.

Specifically, the present invention includes the following features.

[A1] A method for producing soluble thrombomodulin substantially not containing a denatured product of the soluble thrombomodulin that may be generated from the soluble thrombomodulin under acidic conditions, which comprises:
(1) a step of subjecting a soluble thrombomodulin-containing material that contains or is suspected to contain a denatured product of the soluble thrombomodulin to an anion exchanger or hydroxyapatite; and
(2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin.

[A2] The method for producing soluble thrombomodulin substantially not containing a denatured product of the soluble thrombomodulin that may be generated from the soluble thrombomodulin under acidic conditions according to [A1] above, which comprises: (0) a step of leaving the soluble thrombomodulin under acidic conditions of pH 5 or less; (1) a step of subjecting a soluble thrombomodulin-containing material that contains or is suspected to contain a denatured product of the soluble thrombomodulin, which is obtained through the step (0) above, to an anion exchanger or hydroxyapatite; and (2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin.

[A2-2] The method for producing soluble thrombomodulin substantially not containing a denatured product of the soluble thrombomodulin that may be generated from the soluble thrombomodulin under acidic conditions according to [A1] above, which comprises: (*) a step of purifying soluble thrombomodulin; (0) a step of leaving the soluble thrombomodulin under acidic conditions of pH 5 or less; (1) a step of subjecting a soluble thrombomodulin-containing material that contains or is suspected to contain a denatured product of the soluble thrombomodulin, which is obtained through the step (0) above, to an anion exchanger or hydroxyapatite; and (2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin.

[A2-3] The production method according to any one of [A1], [A2], and [A2-2] above, wherein the step of subjecting the soluble thrombomodulin-containing material to an anion exchanger or hydroxyapatite is a step of subjecting the soluble thrombomodulin-containing material to an anion exchanger.

[A2-4] The production method according to any one of [A1], [A2], and [A2-2] above, wherein the step of subjecting the soluble thrombomodulin-containing material to an anion exchanger or hydroxyapatite is a step of subjecting the soluble thrombomodulin-containing material to hydroxyapatite.

[A3] The production method according to any one of [A1] to [A2-4] above, wherein the content of the soluble thrombomodulin is 80% or more with respect to total proteins in the soluble thrombomodulin-containing material.

It is to be noted that, in a case in which cited item numbers are indicated as a range (e.g. [A1] to [A2-4] as described above) and an item having a sub-number such as [A2-2] is disposed in the range, it means that the item having a sub-number such as [A2-2] is also cited. This rule also holds for the following descriptions.

[A3-2] The production method according to any one of [A1] to [A2-4] above, wherein the content of the soluble thrombomodulin is 90% or more with respect to total proteins in the soluble thrombomodulin-containing material.

[A3-3] The production method according to any one of [A1] to [A2-4] above, wherein the content of the soluble thrombomodulin is 95% or more with respect to total proteins in the soluble thrombomodulin-containing material.

[A3-4] The production method according to any one of [A1] to [A2-4] above, wherein the content of the soluble thrombomodulin is 99% or more with respect to total proteins in the soluble thrombomodulin-containing material.

[A4] The production method according to any one of [A1] to [A3-4] above, wherein the step (2) is a step of carrying out linear gradient elution, stepwise gradient elution, or gradient elution in which linear gradient elution is combined with stepwise gradient elution, so as to obtain an elution fraction containing soluble thrombomodulin that does not substantially contain a denatured product of the soluble thrombomodulin.

It is to be noted that, in a case in which cited item numbers are indicated as a range (e.g. [A1] to [A3-4] as described above) and an item having a sub-number such as [A3-2] is disposed in the range, it means that the item having a sub-number such as [A3-2] is also cited. This rule also holds for the following descriptions.

[A5] The production method according to any one of [A1] to [A3-4] above, wherein the step (2) is a step of obtaining a pass-through fraction, in which a fraction containing soluble thrombomodulin that does not substantially contain a denatured product of the soluble thrombomodulin is obtained.

[A6] The production method according to any one of [A1] to [A3-4] above, wherein the step (2) is a step of carrying out isocratic elution to obtain an elution fraction containing soluble thrombomodulin that does not substantially contain a denatured product of the soluble thrombomodulin.

[A7] The production method according to any one of [A1] to [A3-4] above, wherein the step (1) is a step of subjecting the soluble thrombomodulin-containing material to an anion exchanger using a buffer solution of pH 4 to 9; and the step (2) is a step of carrying out linear gradient elution, stepwise gradient elution, or gradient elution in which linear gradient elution is combined with stepwise gradient elution, using a buffer solution of pH 5 to 9 having a salt concentration of 0 to 1M, so as to obtain an elution fraction containing soluble thrombomodulin that does not substantially contain a denatured product of the soluble thrombomodulin, either (a) after the position of a fraction from which the soluble thrombomodulin is eluted has previously been confirmed, or (b) while confirming the presence of the soluble thrombomodulin in the elution fraction.

[A7-2] The production method according to [A7] above, wherein the item (a) is applied from the item (a) or (b).

[A7-3] The production method according to [A7] above, wherein the item (b) is applied from the item (a) or (b).

[A8] The production method according to any one of [A1] to [A3-4] above, wherein the step (1) is a step of subjecting the soluble thrombomodulin-containing material to an anion exchanger using a buffer solution of pH 5 to 8 having a salt concentration of 0.1 to 0.2M; and the step (2) is a step of obtaining a pass-through fraction using a buffer solution of pH 5 to 8 having a salt concentration of 0.1 to 0.2M, so as to obtain a fraction containing soluble thrombomodulin that does not substantially contain a denatured product of the soluble thrombomodulin.

[A9] The production method according to any one of [A1] to [A3-4] above, wherein the step (1) is a step of subjecting the soluble thrombomodulin-containing material to hydroxyapatite using a buffer solution of pH 6 to 9 having a phosphate concentration of 8 mM or less; and the step (2) is a step of carrying out linear gradient elution, stepwise gradient elution, or gradient elution in which linear gradient elution is combined with stepwise gradient elution, using a buffer solution of pH 6 to 9 having a phosphate concentration of 0 to 0.5M, so as to obtain an elution fraction containing soluble thrombomodulin that does not substantially contain a denatured product of the soluble thrombomodulin, either (a) after the position of a fraction from which the soluble thrombomodulin is eluted has previously been confirmed, or (b) while confirming the presence of the soluble thrombomodulin in the elution fraction.

[A9-2] The production method according to [A9] above, wherein the item (a) is applied from the item (a) or (b).

[A9-3] The production method according to [A9] above, wherein the item (b) is applied from the item (a) or (b).

[A10] The production method according to any one of [A1] to [A3-4] above, wherein the step (1) is a step of subjecting the soluble thrombomodulin-containing material to hydroxyapatite using a buffer solution of pH 6 to 9 having a phosphate concentration of 5 to 20 mM or less; and the step (2) is a step of obtaining a pass-through fraction using a buffer solution of pH 6 to 9 having a phosphate concentration of 5 to 20 mM, so as to obtain a fraction containing soluble thrombomodulin that does not substantially contain a denatured product of the soluble thrombomodulin.

[A11] The production method according to any one of [A1] to [A10] above, which does not comprise a step of adjusting the pH of an elution fraction containing soluble thrombomodulin that does not substantially contain a denatured product of the soluble thrombomodulin to pH 4 or less, after the elution fraction has been obtained.

[A12] The production method according to any one of [A1] to [A11] above, which is a production method comprising a concentration step and/or a desalination step, wherein the pH of an elution fraction containing soluble thrombomodulin that does not substantially contain a denatured product of the soluble thrombomodulin is not adjusted to pH 4 or less after the elution fraction has been obtained, wherein the production method is used to convert the soluble thrombomodulin to a pharmaceutical material.

[A13] The production method according to any one of [A1] to [A12] above, wherein the content of a denatured product of soluble thrombomodulin in the soluble thrombomodulin that does not substantially contain the denatured product of soluble thrombomodulin is 3% or less.

[A14] The production method according to any one of [A1] to [A13] above, wherein the soluble thrombomodulin is thrombomodulin obtained from transformant cells prepared by transfecting host cells with DNA encoding the amino acid sequence shown in SEQ ID NO: 9 or 11.

[A15] A method for purifying soluble thrombomodulin in such a way that the soluble thrombomodulin does not substantially contain a denatured product of the soluble thrombomodulin that may be generated from the soluble thrombomodulin under acidic conditions, which comprises (1) a step of subjecting a soluble thrombomodulin-containing material that contains or is suspected to contain a denatured product of the soluble thrombomodulin to an anion exchanger or hydroxyapatite, and (2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin; or the purification method, wherein, in the step of subjecting a soluble thrombomodulin-containing material to an anion exchanger or hydroxyapatite, a buffer solution of the soluble thrombomodulin-containing material is prepared, and the soluble thrombomodulin that does not substantially contain a denatured product of the soluble thrombomodulin is obtained as a pass-through fraction.

[A15-2] The purification method according to [A15] above, which has the characteristic feature according to any one of [A1] to [A14] above.

[A16] The production method according to any one of [A1] to [A15] above, wherein the content of a denatured product of soluble thrombomodulin in the thrombomodulin that does not substantially contain the denatured product of soluble thrombomodulin is 3.0% or less.

[B1] A method for producing thrombomodulin substantially not containing a denatured product of soluble thrombomodulin from a soluble thrombomodulin-containing material that contains or is suspected to contain a denatured product of the soluble thrombomodulin that may be generated from the soluble thrombomodulin under acidic conditions, which comprises (1) a step of subjecting the thrombomodulin-containing material to an anion exchanger or hydroxyapatite and (2) a step of obtaining an elution fraction containing soluble thrombomodulin that does not substantially contain a denatured product of the soluble thrombomodulin under separation conditions in which the soluble thrombomodulin can be separated from the denatured product of the soluble thrombomodulin.

[B2] A method for producing thrombomodulin substantially not containing a denatured product of soluble thrombomodulin from a soluble thrombomodulin-containing material that contains or is suspected to contain a denatured product of the soluble thrombomodulin that may be generated from the soluble thrombomodulin under acidic conditions, which comprises a step of subjecting a soluble thrombomodulin-containing material to an anion exchanger or hydroxyapatite, wherein a buffer solution of the soluble thrombomodulin-containing material is prepared, and the soluble thrombomodulin that does not substantially contain a denatured product of the soluble thrombomodulin is obtained as a pass-through fraction.

[B3] The production method according to [B1] above, wherein the step (1) is a step of subjecting a soluble thrombomodulin-containing material to an anion exchanger, using a buffer solution of pH 4 to 9, and the step (2) is a step of carrying out linear gradient elution, stepwise gradient elution, or gradient elution in which linear gradient elution is combined with stepwise gradient elution, using a buffer solution of pH 5 to 9 having a salt concentration of 0 to 1M, so as to obtain an elution fraction containing soluble thrombomodulin that does not substantially contain a denatured product of the soluble thrombomodulin, after the position of the elution fraction has previously been confirmed, or while confirming the presence of the elution fraction.

[B4] The production method according to [B1] above, wherein the step (1) is a step of subjecting a soluble thrombomodulin-containing material to an anion exchanger, using a buffer solution of pH 4 to 5, and the step (2) is a step of carrying out linear gradient elution, stepwise gradient elution, or gradient elution in which linear gradient elution is combined with stepwise gradient elution, using a buffer solution of pH 5 to 9 having a salt concentration of 0 to 1M, so as to obtain an elution fraction containing soluble thrombomodulin that does not substantially contain a denatured product of the soluble thrombomodulin, after the position of the elution fraction has previously been confirmed, or while confirming the presence of the elution fraction.

[B5] The production method according to [B2] above, wherein a buffer solution of pH 5 to 8 having a salt concentration of 0.1 to 0.2 M is used, and a soluble thrombomodulin-containing material is subjected to an anion exchanger to obtain soluble thrombomodulin substantially not containing a denatured product of the soluble thrombomodulin as a pass-through fraction.

[B6] The production method according to [B1] above, wherein the step (1) is a step of subjecting a soluble thrombomodulin-containing material to hydroxyapatite, using a buffer solution of pH 6 to 9 having a phosphate concentration of 8 mM or less, and the step (2) is a step of carrying out linear gradient elution, stepwise gradient elution, or gradient elution in which linear gradient elution is combined with stepwise gradient elution, using a buffer solution of pH 6 to 9 having a phosphate concentration of 0 to 0.5M, so as to obtain an elution fraction containing soluble thrombomodulin that does not substantially contain a denatured product of the soluble thrombomodulin, after the elution fraction has previously been confirmed, or while confirming the presence of the elution fraction.

[B7] The production method according to [B1] above, wherein the step (1) is a step of subjecting a soluble thrombomodulin-containing material to hydroxyapatite, using a buffer solution of pH 6 to 9 having a phosphate concentration of 1 to 4 mM, and the step (2) is a step of carrying out linear gradient elution, stepwise gradient elution, or gradient elution in which linear gradient elution is combined with stepwise gradient elution, using a buffer solution of pH 6 to 9 having a phosphate concentration of 1 to 40 mM, so as to obtain an elution fraction containing soluble thrombomodulin that does not substantially contain a denatured product of the soluble thrombomodulin, after the elution fraction has previously been confirmed, or while confirming the presence of the elution fraction.

[B8] The production method according to [B2] above, wherein a buffer solution of pH 6 to 9 having a phosphate concentration of 5 to 20 mM is used, and a soluble thrombomodulin-containing material is subjected to hydroxyapatite to obtain soluble thrombomodulin substantially not containing a denatured product of the soluble thrombomodulin as a pass-through fraction.

[B9] The production method according to any one of [B1] to [B8] above, wherein, after an elution fraction containing soluble thrombomodulin that does not substantially contain a denatured product of the soluble thrombomodulin has been obtained, the pH of the elution fraction is not set at pH 4 or less.

[B10] The production method according to any one of [B1] to [B8] above, wherein, after an elution fraction containing soluble thrombomodulin that does not substantially contain a denatured product of the soluble thrombomodulin has been obtained, a concentration step or a desalination step is carried out without setting the pH of the elution fraction at pH 4 or less, so as to convert the soluble thrombomodulin to a pharmaceutical material.

[B11] The production method according to any one of [B1] to [B10] above, wherein the content of a denatured product of soluble thrombomodulin in the soluble thrombomodulin that does not substantially contain the denatured product of soluble thrombomodulin is 3% or less.

[B12] The production method according to any one of [B1] to [B11] above, wherein the content of a denatured product of soluble thrombomodulin in the soluble thrombomodulin that does not substantially contain the denatured product of soluble thrombomodulin is 1% or less.

[B13] The production method according to any one of [B1] to [B12] above, wherein the soluble thrombomodulin is a peptide obtained from transformant cells prepared by transfecting host cells with DNA encoding the amino acid sequence shown in SEQ ID NO: 9 or 11.

Effect of the Invention

The production method of the present invention does not require a concentration step of increasing the concentration of a processed protein. Thus, use of the production method of the present invention enables separation of a denatured product of soluble thrombomodulin from the soluble thrombomodulin, with high productivity, regardless of limitation by a processed volume. As a result, a high-purity soluble thrombomodulin substantially not containing a denatured product of the soluble thrombomodulin can be obtained.

BEST MODE FOR CARRYING OUT THE INVENTION

The thrombomodulin used in the present invention has been known to have action to (1) selectively bind to thrombin and to (2) promote the activation of protein C caused by the thrombin. In addition, it is preferable that the present thrombomodulin generally have (3) action to extend the coagulation time by thrombin and/or (4) action to suppress the platelet aggregation caused by thrombin. Such action of thrombomodulin may be referred to as thrombomodulin activity.

As such thrombomodulin activity, thrombomodulin preferably has the actions in (1) and (2) above, and more preferably has all the actions in (1) to (4) above.

As the action to promote the activation of protein C caused by thrombin, the activity level of the action to promote the activation of protein C or the presence of absence of such action can easily be confirmed by applying the test methods clearly described in various types of known publications including JP Patent Publication (Kokai) No. 64-6219 A (1989). Moreover, the action to extent the coagulation time caused by thrombin or the action to suppress the platelet aggregation caused by thrombin can also be confirmed in the same above manner.

An example of the soluble thrombomodulin described in the present invention is soluble thrombomodulin that is soluble in water in the absence of a surfactant. As a preferred example of the solubility of such soluble thrombomodulin is a solubility of 1 mg/ml or more, or 10 mg/ml or more in water, for example, in distilled water used for injection (in general, around a neutral range in the absence of a surfactant such as Triton X-100 or Polidocanol). Such solubility is preferably 15 mg/ml or more, or 17 mg/ml or more; more preferably 20 mg/ml or more, 25 mg/ml or more, or 30 mg/ml or more; and particularly preferably 60 mg/ml or more. In some cases, such solubility may be 80 mg/ml or more, or 100 mg/ml or more. In order to determine whether or not soluble thrombomodulin was dissolved, after the soluble thrombomodulin has been dissolved, the solution is observed by the naked eye, for example, directly below white light source, at a position of brightness of approximately 1,000 lux. When the solution is clear and does not contain insoluble substances that are clearly seen, it can be understood as a clear indicator of dissolution of the soluble thrombomodulin. In addition, it is also possible to filtrate the solution and to confirm the presence or absence of a residue.

The thrombomodulin used in the present invention preferably comprises an amino acid sequence consisting of amino acids at positions 19 to 132 of the amino acid sequence as shown in SEQ ID NO: 1, which has been known as the central portion of the thrombomodulin activity of human thrombomodulin. The amino acid sequence of the present thrombomodulin is not particularly limited, as long as it comprises an amino acid sequence consisting of amino acids at positions 19 to 132 of the amino acid sequence as shown in SEQ ID NO: 1. The amino acid sequence consisting of amino acids at positions 19 to 132 of the above-described amino acid sequence as shown in SEQ ID NO: 1 may be naturally or artificially mutated, as long as it has action to promote the activation of protein C caused by thrombin, namely, thrombomodulin activity. That is to say, the amino acid sequence consisting of amino acids at positions 19 to 132 may comprise a substitution, deletion, or addition of one or multiple amino acids with respect to the amino acid sequence as shown in SEQ ID NO: 1. The acceptable level of mutation is not particularly limited, as long as the aforementioned amino acid sequence has thrombomodulin activity. The mutated amino acid sequence consisting of amino acids at positions 19 to 132 of the amino acid sequence as shown in SEQ ID NO: 1 shows homology of, for example, 50% or more, preferably 70% or more, more preferably 80% or more, further preferably 90% or more, particularly preferably 95% or more, and most preferably 98% or more, with the original amino acid sequence. Such an amino acid sequence is referred to as a homologous mutation sequence. As described later, such a mutated amino acid sequence can be easily produced by a common genetic engineering technique.

In the amino acid sequence as shown in SEQ ID NO: 3, Val that is the amino acid at position 125 of the amino acid sequence as shown in SEQ ID NO: 1 has been substituted with Ala. The thrombomodulin used in the present invention also preferably includes an amino acid sequence consisting of amino acids at positions 19 to 132 of the amino acid sequence as shown in SEQ ID NO: 3.

Thus, the type of the thrombomodulin used in the present invention is not particularly limited, as long as it has, at least, an amino acid sequence consisting of amino acids at positions 19 to 132 of the amino acid sequence as shown in SEQ ID NO: 1 or 3, or a homologous mutation sequence of the aforementioned sequence, and it comprises at least a peptide sequence having thrombomodulin activity. Preferred examples of the present thrombomodulin include a peptide consisting of a sequence consisting of amino acids at positions 19 to 132 or at positions 17 to 132 of the amino acid sequence as shown in SEQ ID NO: 1 or 3, and a peptide consisting of a homologous mutation sequence of the aforementioned sequence and having at least thrombomodulin activity. A peptide consisting of a sequence consisting of amino acids at positions 19 to 132 of the amino acid sequence as shown in SEQ ID NO: 1 or 3 is more preferable. Moreover, in another more preferred embodiment, there can also be applied a peptide consisting of a homologous mutation sequence of the amino acid sequence consisting of amino acids at positions 19 to 132 or at positions 17 to 132 of the amino acid sequence as shown in SEQ ID NO: 1 or 3 and having at least thrombomodulin activity.

In another embodiment, the thrombomodulin used in the present invention preferably comprises an amino acid sequence consisting of amino acids at positions 19 to 480 of the amino acid sequence as shown in SEQ ID NO: 5. The type of the present thrombomodulin in this embodiment is not particularly limited, as long as it comprises such an amino acid sequence consisting of amino acids at positions 19 to 480 of the amino acid sequence as shown in SEQ ID NO: 5. The amino acid sequence consisting of amino acids at positions 19 to 480 of the aforementioned amino acid sequence as shown in SEQ ID NO: 5 may be homologously mutated, as long as it has action to promote the activation of protein C caused by thrombin, namely, thrombomodulin activity.

In the amino acid sequence as shown in SEQ ID NO: 7, Val that is the amino acid at position 473 of the amino acid sequence as shown in SEQ ID NO: 5 has been substituted with Ala. The thrombomodulin used in the present invention also preferably includes an amino acid sequence consisting of amino acids at positions 19 to 480 of the amino acid sequence as shown in SEQ ID NO: 7.

Thus, the type of the thrombomodulin used in the present invention is not particularly limited, as long as it has, at least, an amino acid sequence consisting of amino acids at positions 19 to 480 of the amino acid sequence as shown in SEQ ID NO: 5 or 7, or a homologous mutation sequence of the aforementioned sequence, and it comprises at least a peptide sequence having thrombomodulin activity. Preferred examples of the present thrombomodulin include a peptide consisting of a sequence consisting of amino acids at positions 19 to 480 or at positions 17 to 480 of the amino acid sequence as shown in SEQ ID NO: 5 or 7, and a peptide consisting of a homologous mutation sequence of the aforementioned sequence and having at least thrombomodulin activity. A peptide consisting of a sequence consisting of amino acids at positions 19 to 480 of the amino acid sequence as shown in SEQ ID NO: 5 or 7 is more preferable. Moreover, in a further more preferred embodiment, there can also be applied a peptide consisting of a homologous mutation sequence of the amino acid sequence consisting of amino acids at positions 19 to 480 or at positions 17 to 480 of the amino acid sequence as shown in SEQ ID NO: 5 or 7 and having at least thrombomodulin activity.

In a further embodiment, the thrombomodulin used in the present invention preferably includes an amino acid sequence consisting of amino acids at positions 19 to 515 of the amino acid sequence as shown in SEQ ID NO: 9. The type of the present thrombomodulin in this embodiment is not particularly limited, as long as it comprises such an amino acid sequence consisting of amino acids at positions 19 to 515 of the amino acid sequence as shown in SEQ ID NO: 9. The amino acid sequence consisting of amino acids at positions 19 to 515 of the aforementioned amino acid sequence as shown in SEQ ID NO: 9 may be homologously mutated, as long as it has action to promote the activation of protein C caused by thrombin, namely, thrombomodulin activity.

In the amino acid sequence as shown in SEQ ID NO: 11, Val that is the amino acid at position 473 of the amino acid sequence as shown in SEQ ID NO: 9 has been substituted with Ala. The thrombomodulin used in the present invention also preferably includes an amino acid sequence consisting of amino acids at positions 19 to 515 of the amino acid sequence as shown in SEQ ID NO: 11.

Thus, the type of the thrombomodulin used in the present invention is not particularly limited, as long as it has, at least, an amino acid sequence consisting of amino acids at positions 19 to 515 of the amino acid sequence as shown in SEQ ID NO: 9 or 11, or peptide sequence having a homologous mutation sequence of the aforementioned sequence and having at least thrombomodulin activity. More preferred examples of the present thrombomodulin include a peptide consisting of a sequence consisting of amino acids at positions 19 to 516, at positions 19 to 515, at positions 17 to 516, or at positions 17 to 515 of the amino acid sequence as shown in SEQ ID NO: 9 or 11, and a peptide consisting of a homologous mutation sequence of the aforementioned sequence and having at least thrombomodulin activity. A peptide consisting of a sequence consisting of amino acids at positions 19 to 516, at positions 19 to 515, at positions 17 to 516, or at positions 17 to 515 of the amino acid sequence as shown in SEQ ID NO: 9 is particularly preferable. In addition, a mixture thereof is also a preferred example. Moreover, in another particularly preferred embodiment, there can also be applied a peptide consisting of a sequence consisting of amino acids at positions 19 to 516, at positions 19 to 515, at positions 17 to 516, or at positions 17 to 515 of the amino acid sequence as shown in SEQ ID NO: 11. A mixture thereof is also a preferred example of the thrombomodulin of the present invention. Further, a peptide consisting of a homologous mutation sequence thereof and having at least thrombomodulin activity is also another preferred example of the present thrombomodulin.

A peptide having a homologous mutation sequence is as described above. Such a peptide having a homologous mutation sequence also includes a peptide that may comprise a substitution, deletion, or addition of one or more, namely; one or multiple, and preferably several (for example, 1 to 20, preferably 1 to 10, more preferably 1 to 5, and particularly preferably 1 to 3) amino acids in the amino acid sequence of the target peptide. The acceptable level of mutation is not particularly limited, as long as the peptide has thrombomodulin activity. The mutated peptide shows homology of, for example, 50% or more, preferably 70% or more, more preferably 80% or more, further preferably 90% or more, particularly preferably 95% or more, and most preferably 98% or more, at the amino acid sequence level with the target peptide.

Moreover, other preferred examples of the thrombomodulin used in the present invention include a peptide consisting of a sequence (462 amino acid residues) as shown in SEQ ID NO: 14, a peptide consisting of a sequence (272 amino acid residues) as shown in SEQ ID NO: 8, and a peptide consisting of a sequence (236 amino acid residues) as shown in SEQ ID NO: 6, which are described in JP Patent Publication (Kokai) No. 64-6219 (1989) A.

The type of the thrombomodulin used in the present invention is not particularly limited, as long as it has at least an amino acid sequence consisting of amino acids at positions 19 to 132 of the amino acid sequence as shown in SEQ ID NO: 1 or 3. Among others, a peptide having at least an amino acid sequence consisting of amino acids at positions 19 to 480 of the amino acid sequence as shown in SEQ ID NO: 5 or 7 is preferable, and a peptide having at least an amino acid sequence consisting of amino acids at positions 19 to 515 of the amino acid sequence as shown in SEQ ID NO: 9 or 11 is more preferable. A more preferred example of the peptide having at least an amino acid sequence consisting of amino acids at positions 19 to 515 of the amino acid sequence as shown in SEQ ID NO: 9 or 11 is a peptide consisting of a sequence consisting of amino acids at positions 19 to 516, at positions 19 to 515, at positions 17 to 516, or at positions 17 to 515 of the amino acid sequence as shown in SEQ ID NO: 9 or 11. Furthermore, a mixture obtained from such peptides each consisting of a sequence consisting of amino acids at positions 19 to 516, at positions 19 to 515, at positions 17 to 516, or at positions 17 to 515 of the amino acid sequence as shown in SEQ ID NO: 9 or 11 is also a preferred example of the thrombomodulin of the present invention.

In the case of the aforementioned mixture, the mixing ratio between a peptide that starts from position 17 of the amino acid sequence as shown in SEQ ID NO: 9 or 11 and a peptide that starts from position 19 thereof is (30:70) to (50:50), and preferably (35:65) to (45:55).

Moreover, the mixing ratio between a peptide that terminates at position 515 of the amino acid sequence as shown in SEQ ID NO: 9 or 11 and a peptide that terminates at position 516 is (0:100) to (90:10), and may be (70:30) to (90:10), or may be (0:100) to (30:70).

The mixing ratio of such peptides can be obtained by a common method.

It is to be noted that the sequence consisting of amino acids at positions 19 to 132 of the amino acid sequence as shown in SEQ ID NO: 1 corresponds to the sequence consisting of amino acids at positions 367 to 480 of the amino acid sequence as shown in SEQ ID NO: 9, and that the sequence consisting of amino acids at positions 19 to 480 of the amino acid sequence as shown in SEQ ID NO: 5 corresponds to the sequence consisting of amino acids at positions 19 to 480 of the amino acid sequence as shown in SEQ ID NO: 9.

Further, the sequence consisting of amino acids at positions 19 to 132 of the amino acid sequence as shown in SEQ ID NO: 3 corresponds to the sequence consisting of amino acids at positions 367 to 480 of the amino acid sequence as shown in SEQ ID NO: 11, and the sequence consisting of amino acids at positions 19 to 480 of the amino acid sequence as shown in SEQ ID NO: 7 corresponds to the sequence consisting of amino acids at positions 19 to 480 of the amino acid sequence as shown in SEQ ID NO: 11.

Still further, the sequences each consisting of amino acids at positions 1 to 18 of the amino acid sequences as shown in SEQ ID NOS: 1, 3, 5, 7, 9, and 11 are all identical to one another.

As described below, the thrombomodulin used in the present invention can be obtained from transformant cells that are prepared by incorporating DNA encoding the peptide having the amino acid sequence as shown in SEQ ID NO: 1, 3, 5, 7, 9, 11, etc. (specifically, the nucleotide sequence as shown in SEQ ID 2, 4, 6, 8, 10, 12, etc., respectively) into a vector and then by transfecting host cells with the vector. As thrombomodulin used herein, thrombomodulin obtained from transformant cells prepared by transfecting host cells with a vector comprising DNA encoding the amino acid sequence shown in SEQ ID NO: 9 or 11 (specifically the DNA shown in SEQ ID NO: 10 or 12, respectively) is preferable.

It is only necessary that such peptides have the aforementioned amino acid sequences. Thus, a sugar chain may be or may not be added. Addition of a sugar chain is not particularly limited. In addition, in genetic engineering techniques, the type of such a sugar chain, a position to which a sugar chain is added, and the level of addition differ depending on the type of host cell used, and they are not particularly limited. The binding position of such a sugar chain and the type thereof are described in JP Patent Publication (Kokai) No. 11-341990 (1999) A. In the case of the thrombomodulin of the present invention, the same sugar chain may be added to the same position as those described in the aforementioned publication. As described later, the method for obtaining the thrombomodulin of the present invention is not limited to genetic engineering. In the case of obtaining the present thrombomodulin by genetic engineering, however, as a signal sequence that can be used in expression, a nucleotide sequence encoding the amino acid sequence consisting of amino acids at positions 1 to 18 of the aforementioned amino acid sequence as shown in SEQ ID NO: 9, a nucleotide sequence encoding the amino acid sequence consisting of amino acids at positions 1 to 16 of the aforementioned amino acid sequence as shown in SEQ ID NO: 9, and other known signal sequences such as the signal sequence of a human tissue plasminogen activator can be used (International Publication WO88/9811, and JP Patent Publication (Kokai) No. 11-341990 (1999) A).

When a DNA sequence encoding thrombomodulin is introduced into host cells, there is preferably applied a method, which comprises incorporating the DNA sequence encoding thrombomodulin into a vector, and more preferably into an expression vector capable of expressing in animal cells, and then introducing the vector into the host cells. Such an expression vector is a DNA molecule that is constituted with a promoter sequence, a sequence for adding a ribosome binding site to mRNA, a DNA sequence encoding a protein to be expressed, a splicing signal, a terminator sequence for transcription termination, a replication origin sequence, and others. Examples of a preferred animal cell expression vector include: pSV2-X reported by R. C. Mulligan et al. [Proc. Natl. Acad. Sci. U.S.A. 78, 2072 (1981)]; and pBP69T (69-6) reported by P. M. Howley et al. [Methods in Emzymology, 101, 387, Academic Press (1983)].

Examples of host cells that can be used in production of such peptides include Chinese hamster ovary (CHO) cells, COS-1 cells, COS-7 cells, VERO (ATCC CCL-81) cells, BHK cells, canine kidney-derived MDCK cells, and hamster AV-12-664 cells. In addition, examples of such host cells derived from human cells include HeLa cells, WI38 cells, and human 293 cells. Of these cells, CHO cells are extremely common and preferable. Among CHO cells, DHFR-CHO cells are more preferable.

In a genetic engineering process or a peptide production process, microorganisms such as *Escherichia coli* are often used. A host-vector system suitable for each process is preferably used. An adequate vector system can be selected even depending on the aforementioned host cells. A thrombomodulin gene used in a genetic recombination technique has been cloned. Examples of producing thrombomodulin by such a genetic recombination technique have been disclosed.

Further, a method for purifying thrombomodulin to obtain a purified product has also been known [JP Patent Publication (Kokai) Nos. 64-6219 (1989) A, 2-255699 (1990) A, 5-213998 (1993) A, 5-310787 (1993) A, and 7-155176 (1995) A; and J. Biol. Chem., 264: 10351-10353 (1989)]. Accordingly, the thrombomodulin used in the present invention can be produced by the methods described in the aforementioned reports, or by methods equivalent thereto. For example, JP Patent Publication (Kokai) No. 64-6219 (1989) A discloses the Escherichia coli K-12 strain DH5 (ATCC Accession No. 67283) comprising a plasmid pSV2TMJ2 containing DNA encoding the full-length thrombomodulin. A strain (Escherichia coli DH5/pSV2TM J2) (FERM BP-5570), wherein the aforementioned strain has been re-deposited with the former National Institute of Bioscience and Human-Technology (the current National Institute of Advanced Industrial Science and Technology, an Independent Administrative Institution under the Ministry of Economy, Trade and Industry (AIST)), can also be used. The thrombomodulin of the present invention can be prepared by a known genetic engineering technique using the DNA encoding the full-length thrombomodulin as a raw material.

The thrombomodulin used in the present invention may be prepared by a conventionally known method or a method equivalent thereto. For example, the present thrombomodulin can be prepared with reference to the aforementioned method of Yamamoto et al. [JP Patent Publication (Kokai) No. 64-6219 A (1989)] or the method described in JP Patent Publication (Kokai) No. 5-213998 A (1993). That is to say, a human-derived thrombomodulin gene may be subjected to genetic engineering to convert it to DNA encoding the amino acid sequence as shown in SEQ ID NO: 9, for example, and it may be further modified, as necessary. For such modification, a codon encoding the amino acid at position 473 of the amino acid sequence as shown in SEQ ID NO: 9 (particularly, the nucleotide at position 1418) is subjected to site-directed mutagenesis according to the method described in Method in Enzymology, 100: 468 (1983), Academic Press, so as to obtain DNA encoding the amino acid sequence as shown in SEQ ID NO: 11 (which specifically consists of the nucleotide sequence as shown in SEQ ID NO: 12), for example. Using synthetic DNA used for mutation that has the nucleotide sequence as shown in SEQ ID NO: 13, the nucleotide T at position 1418 of SEQ ID NO: 10 may be converted to the nucleotide C, so as to obtain mutated DNA, for example.

The thus prepared DNA is incorporated into, for example, Chinese hamster ovary (CHO) cells to obtain transformant cells. Such cells are then selected, as appropriate. The selected cells are then cultured to obtain a culture solution, and thrombomodulin can be produced from the culture solution by purifying it according to a known method. As stated above, it is preferable that the aforementioned host cells be transfected with the DNA (SEQ ID NO: 10) encoding the amino acid sequence as shown in SEQ ID NO: 9. A method for producing the thrombomodulin used in the present invention is not limited to the aforementioned method. For example, such thrombomodulin may be extracted and purified also from urine, blood, other types of body fluids, etc. Otherwise, it may also be extracted and purified from tissues producing thrombomodulin, a culture solution of such tissues, etc. Further, the thrombomodulin may be further subjected to a cleavage treatment using protease, as necessary.

When the thrombomodulin of the present invention is produced by the aforementioned cell culture method, there may be cases where the N-terminal amino acid becomes diversified as a result of posttranslational modification of protein. For example, the amino acids at positions 17, 18, 19, or 22 of SEQ ID NO: 9 may become the N-terminus in some cases. In addition, there may also be cases where the N-terminal amino acid is modified such that the glutamic acid at position 22 could be converted to pyroglutamic acid. It is preferable that the amino acid at position 17 or 19 become the N-terminus. It is more preferable that the amino acid at position 19 become the N-terminus. Moreover, in another preferred embodiment, the amino acid at position 17 may become the N-terminus. With regard to the aforementioned modification, diversification, etc., the same holds true for SEQ ID NO: 11.

Furthermore, when the thrombomodulin of the present invention is produced using DNA having the nucleotide sequence as shown in SEQ ID NO: 10, the C-terminal amino acid may become diversified, and as a result, a peptide that is shorter than the ordinary peptide by one amino acid residue may be produced in some cases. That is, there may be cases where the amino acid at position 515 becomes the C-terminus, and it is further amidated, so that the C-terminal amino acid can be modified. As a result, a peptide with diversified N-terminal amino acid and C-terminal amino acid, or a mixture thereof, may be produced. The amino acid at position 515 may preferably become the C-terminus. Moreover, in another preferred embodiment, the amino acid at position 516 may become the C-terminus. With regard to the aforementioned modification, diversification, etc., the same holds true for DNA having the nucleotide sequence as shown in SEQ ID NO: 12.

The thrombomodulin obtained by the aforementioned method may be a peptide mixture with diversified N-terminus and C-terminus. A specific example is a mixture of peptides consisting of a sequence consisting of amino acids at positions 19 to 516, at positions 19 to 515, at positions 17 to 516, or at positions 17 to 515 of the amino acid sequence as shown in SEQ ID NO: 9.

The present invention provides a method for producing soluble thrombomodulin substantially not containing a denatured product of the soluble thrombomodulin that may be generated from the soluble thrombomodulin under acidic conditions. The present production method is not particularly limited, as long as it comprises (1) a step of subjecting a soluble thrombomodulin-containing material that contains or is suspected to contain a denatured product of the soluble thrombomodulin to an anion exchanger or hydroxyapatite and (2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin. However, this production method preferably comprises (0) a step of leaving soluble thrombomodulin under acidic conditions of pH 5 or less, before the step (1), and it more preferably comprises (0) a step of leaving soluble thrombomodulin under acidic conditions of pH 5 or less and (*) a step of purifying soluble thrombomodulin, before the step (1). The time point at which the step (*) is carried out is not particularly limited in the production method of the present invention. The step (*) is preferably carried out before the step (1).

Acidic conditions under which a denatured product of soluble thrombomodulin may be generated from the soluble thrombomodulin in the present invention include, for example, pH 5 or less, preferably pH 4 or less, and more preferably pH 3 or less. The lower limit of such pH is, for example, pH 1 or more, preferably pH 2 or more, and more preferably pH 3 or more. In addition, the time required under such acidic conditions is, for example, 0.5 hours or more, preferably 1 hour or more, and more preferably 2 hours or more. Moreover, the temperature applied under such acidic conditions is, for example, room temperature, preferably 15° C. or lower, and more preferably 8° C. or lower. The lower limit of such temperature is generally 0° C. or higher, preferably 2° C. or higher, and more preferably 5° C. or higher. Under the aforementioned acidic conditions, soluble thrombomodulin is present in the form of a mixture of the soluble thrombomodulin and a denatured product thereof.

The upper limit of the content of a denatured product of soluble thrombomodulin in the "thrombomodulin substantially not containing the denatured product of soluble thrombomodulin" produced by the method of the present invention is preferably 3.0% or less, more preferably 2.0% or less, further preferably 1.0% or less, and particularly preferably 0.5% or less. The lower limit of the aforementioned content is 0.01% or more. However, it is preferably a detection limit or less. The content percentage of a denatured product of soluble thrombomodulin can be measured by chromatography. For example, 150 μl of an analytical sample is subjected to an analytical size exclusion chromatography, TSK-GEL G3000SWXL (7.8 mm I.D.×30 cm; TOSOH). A mobile phase of a phosphate buffer containing sodium sulfate is used, and the absorbance at 280 nm is measured at a flow rate of 0.9 ml/min. Thus, the content percentage can be obtained based on the peak area of the soluble thrombomodulin.

When 150 μl of an analytical sample is subjected to an analytical size exclusion chromatography, TSK-GEL G3000SWXL (7.8 mm I.D.×30 cm; TOSOH), using a mobile phase of a phosphate buffer containing sodium sulfate, and analysis is then conducted at a flow rate of 0.9 ml/min, a denatured product of soluble thrombomodulin that may be generated from the soluble thrombomodulin of the present invention under acidic conditions is detected at a retention time of approximately 90% of the retention time of the soluble thrombomodulin. (When the retention time of the soluble thrombomodulin is approximately 9 minutes, for example, the retention time of a denatured product of the soluble thrombomodulin is approximately 8 minutes.) Furthermore, in an electrophoretic method (Native-PAGE), such denatured product of soluble thrombomodulin that may be generated from the soluble thrombomodulin of the present invention under acidic conditions moved, and it was observed on the high molecular weight side of thrombomodulin. In SDS-PAGE, such denatured product was not detected.

The kind of the soluble thrombomodulin-containing material used in the present invention, which contains or is suspected to contain a denatured product of soluble thrombomodulin that may be generated under acidic conditions (hereinafter abbreviated as a "denatured product-containing material" at times), is not particularly limited, so long as it contains a soluble thrombomodulin and a denatured product of soluble thrombomodulin. An example of such soluble thrombomodulin-containing material is a soluble thrombomodulin solution obtained from a culture supernatant prepared by culturing cells capable of producing soluble thrombomodulin in a serum component-containing medium or a serum free medium. Preferred examples of such soluble thrombomodulin-containing material include: a soluble thrombomodulin solution obtained by performing a purification step on a culture supernatant prepared by culturing cells capable of producing soluble thrombomodulin in a serum component-containing medium or a serum free medium; and a soluble thrombomodulin solution left under acidic conditions after preparing the aforementioned culture supernatant. A more preferred example of such soluble thrombomodulin-containing solution is a soluble thrombomodulin solution obtained by performing a purification step on a culture supernatant prepared by culturing cells capable of producing soluble thrombomodulin in a serum component-containing medium or a serum free medium. Further, in another embodiment of the present invention, a soluble thrombomodulin solution left under acidic conditions after preparing the aforementioned culture supernatant is preferable.

The aforementioned purification step is not particularly limited, as long as it is able to eliminate at least proteins other than soluble thrombomodulin. Examples of such purification step include a step of eluting and recovering soluble thrombomodulin under acidic conditions, using affinity chromatography in which an antibody reacting with thrombomodulin is supported, and a step of allowing the soluble thrombomodulin obtained by the aforementioned affinity chromatography to come into contact with a cation exchanger under conditions consisting of a specific conductivity of 25 to 34 ms/cm and pH 3 to 4, so as to recover the soluble thrombomodulin as a pass through fraction.

The aforementioned soluble thrombomodulin-containing material (denatured product-containing material) is not particularly limited, as long as it contains soluble thrombomodulin and a denatured product of the soluble thrombomodulin. An example of such soluble thrombomodulin-containing material is a material that does not substantially contain proteins other than soluble thrombomodulin and a denatured product of the soluble thrombomodulin. Specifically, the lower limit of the content of soluble thrombomodulin with respect to total proteins in such soluble thrombomodulin-containing material is, for example, 50% or more, preferably 60% or more, more preferably 70% or more, further preferably 80% or more, particularly preferably 90% or more, extremely preferably 95% or more, and most preferably 99% or more. In addition, there may be cases in which the content of 99.9% or more is preferable. The aforementioned content of soluble thrombomodulin generally indicates the content of soluble thrombomodulin itself. However, there may also be cases in which such content means the contents of both soluble thrombomodulin and a denatured product of the soluble thrombomodulin. Even in a case in which the content of soluble thrombomodulin means the contents of both soluble thrombomodulin and a denatured product of the soluble thrombomodulin, the lower limit of the content of soluble thrombomodulin with respect to total proteins in such soluble thrombomodulin-containing material is, for example, 50% or more, preferably 60% or more, more preferably 70% or more, further preferably 80% or more, particularly preferably 90% or more, extremely preferably 95% or more, and most preferably 99% or more. In addition, there may also be cases in which the content of 99.9% or more is preferable.

The aforementioned content of soluble thrombomodulin can be measured using chromatography. For example, an analytical reverse phase chromatography, Asahipak C4P-50 (4.6 mm I.D.×15 cm; Showa Denko K. K.) is employed, and 150 μl of an analytical sample is subjected at a flow rate of 0.8 ml/min, using a mobile phase consisting of distilled water containing 0.1% trifluoroacetic acid (liquid A) and acetonitrile containing 0.1% trifluoroacetic acid (liquid B). The mixing ratio of liquid A and liquid B is linearly changed from 96:4 to 0:100 (48 minutes later). Thereafter, the absorbance at 280 nm of an eluate is measured and analyzed. Thus, the content of soluble thrombomodulin can be obtained based on the peak areas of the soluble thrombomodulin and other proteins. Alternatively, the quantities of proteins other than soluble thrombomodulin are measured by the ELISA method described in JP Patent Publication (Kokai) No. 11-341990 A (1999), so that the content of the soluble thrombomodulin can be obtained.

In the present invention, after performing a step of leaving thrombomodulin under acidic conditions of pH 5 or less, a material containing such thrombomodulin that contains or is suspected to contain a denatured product of the soluble thrombomodulin is preferably subjected to an anion exchanger or hydroxyapatite. The upper limit of such acidic conditions is preferably pH 5 or less, more preferably pH 4 or less, and further preferably pH 3 or less. The lower limit thereof is preferably pH 1 or more, more preferably pH 2 or more, and further preferably pH 3 or more.

In addition, the time required under such acidic conditions is, for example, 0.5 hours or more, preferably 1 hour or more, and more preferably 2 hours or more. Moreover, the temperature applied under such acidic conditions is, for example, room temperature, preferably 15° C. or lower, and more preferably 8° C. or lower. The lower limit of such temperature is generally 0° C. or higher, preferably 2° C. or higher, and more preferably 5° C. or higher.

A preferred salt used in the present invention is a chloride. The most preferred salt is sodium chloride. In addition, preferred phosphates in hydroxyapatite are sodium phosphate and potassium phosphate.

Separation conditions for separating soluble thrombomodulin from a denatured product of the soluble thrombomodulin include: linear gradient elution conditions; stepwise gradient elution conditions; gradient elution conditions in which linear gradient elution is combined with stepwise gradient elution; conditions in which soluble thrombomodulin is eluted from a pass-through fraction; and isocratic elution conditions. Of these conditions, linear gradient elution conditions, stepwise gradient elution conditions, gradient elution conditions in which linear gradient elution is combined with stepwise gradient elution, and conditions in which soluble thrombomodulin is eluted from a pass-through fraction are preferable. Further, linear gradient elution conditions, stepwise gradient elution conditions, and gradient elution conditions in which linear gradient elution is combined with stepwise gradient elution are more preferable. Furthermore, in another embodiment, conditions in which soluble thrombomodulin is eluted from a pass-through fraction are preferable. Still further, there may also be a case in which isocratic conditions are preferable.

As a pass-through fraction, there is a fraction in which soluble thrombomodulin is not adsorbed on an anion exchanger or hydroxyapatite when a soluble thrombomodulin-containing material is subjected to such anion exchanger or hydroxyapatite. The kind of such pass-through fraction is not particularly limited, as long as it does not substantially contain a denatured product of thrombomodulin. For example, a fraction of 1 to 20 column volumes, 1 to 50 column volumes, or 1 to 100 column volumes may be used.

Gradient elution conditions may be determined, as appropriate, depending on the type of a column used. Specific conditions will be described later. In addition, for conditions in which soluble thrombomodulin is eluted from a pass-through fraction, a buffer solution to be used may be determined, as appropriate, depending on the type of a column used. Specific conditions will be described later. Moreover, isocratic elution conditions may be determined, as appropriate, depending on the type of a column used.

As an anion exchanger, an anion exchanger having a quaternary ammonium group such as SourceQ (GE Healthcare Bio-Sciences), which is a strong anion exchanger, is preferably used. Before subjecting a denatured product-containing material thereto, such anion exchanger may be equilibrated with several column volumes of a buffer solution of pH 4 to 9 (the kind of such buffer solution is not limited; for example, a 0.1M acetate buffer (pH 4), a 0.02M phosphate buffer (pH 7.3), or a 0.02M Tris buffer (pH 8)). After completion of such equilibration, a denatured product-containing material is subjected to the anion exchanger. Before elution of soluble thrombomodulin, the anion exchanger may be washed with a buffer solution of pH 4 to 9 (the kind of such buffer solution is not limited; for example, a 0.1M acetate buffer (pH 4), a 0.02M phosphate buffer (pH 7.3), or a 0.02M Tris buffer (pH 8)). With regard to the adsorbed denatured product-containing material, soluble thrombomodulin may be separated from a denatured product of the soluble thrombomodulin and may be eluted by gradient elution with a salt concentration of 0 to 1M, using a buffer solution of pH 5 to 9, and preferably of pH 7 to 8 (the kind of such buffer solution is not limited; for example, a 0.02M phosphate buffer (pH 7.3) or a 0.02M Tris buffer (pH 8)). Separation conditions are not particularly limited, as long as they are conditions capable of separating soluble thrombomodulin from a denatured product of the soluble thrombomodulin and eluting them. Examples of such gradient elution conditions include linear gradient elution conditions, stepwise gradient elution conditions, and gradient elution conditions in which linear gradient elution is combined with stepwise gradient elution. In such gradient elution, a salt concentration is set at preferably 0 to 0.3M, and more preferably 0.03 to 0.26M. The amount of a buffer solution used in elution is 2 to 40 column volumes, and preferably 5 to 20 column volumes.

When gradient elution conditions are used, as a step of obtaining an elution fraction containing soluble thrombomodulin that does not substantially contain a denatured product of the soluble thrombomodulin, there is applied, for example, (a) a step of obtaining such elution fraction after the position of a fraction from which the soluble thrombomodulin is eluted has previously been confirmed, or (b) a step of obtaining such elution fraction while confirming the presence of the soluble thrombomodulin in the elution fraction.

Specifically describing the step (a), the position of an elution fraction that does not substantially contain a denatured product of soluble thrombomodulin has previously been confirmed by an analytic method for confirming the presence of soluble thrombomodulin and that of a denatured product of the soluble thrombomodulin (for example, size exclusion chromatography described in Example 7 later), and the elution fraction at the position is recovered. On the other hand, specifically describing the step (b), while confirming by an analytic method for confirming the presence of soluble thrombomodulin and that of a denatured product of the soluble thrombomodulin (for example, size exclusion chromatography described in Example 7 later) that an elution fraction contains soluble thrombomodulin and does not substantially contain a denatured product of the soluble thrombomodulin, such elution fraction containing soluble thrombomodulin and substantially not containing a denatured product of the soluble thrombomodulin is obtained. The step (b) is preferable. In addition, there may also be cases in which the step (a) is preferable.

Moreover, soluble thrombomodulin substantially not containing a denatured product thereof can also be obtained as a pass-through fraction by substituting a denatured product-containing material with a suitable buffer solution before subjecting such denatured product-containing material to an anion exchanger. Such pass-through fraction is a fraction in which soluble thrombomodulin is not adsorbed on the anion exchanger when a soluble thrombomodulin-containing material is subjected to the anion exchanger. A difference between soluble thrombomodulin and a denatured product thereof in terms of adsorbability on a column is utilized. In this case, as an anion exchanger, an anion exchanger having a quaternary ammonium group such as SourceQ, Q Sepharose FF (GE Healthcare Bio-Sciences), Sartobind (Sartorius K.K.) or Mustang (PALL), which is a strong anion exchanger, is preferably used. A suitable buffer solution used in substitution is preferably a buffer solution of pH 5 to 8 having a salt concentration of 0.1 to 0.2M. The kind of such buffer solution is not limited. For example, 0.02M phosphate, 0.18M sodium chloride, pH 7.3 can be used. As a method of obtaining a pass-through fraction, while confirming by an analytic method such as size exclusion chromatography described in Example 7 later that an elution fraction contains soluble thrombomodulin and does not substantially contain a denatured product of the soluble thrombomodulin, such fraction may be appropriately obtained.

Moreover, isocratic elution conditions may also be used. In this case as well, such conditions may be determined, as appropriate, with reference to gradient elution conditions and conditions under which soluble thrombomodulin is eluted from a pass-through fraction.

As hydroxyapatite, Macro-Prep (R) Ceramic Hydroxyapatite TYPE 1 (BIO-RAD) is used, for example. Before subjecting a denatured product-containing material thereto, such hydroxyapatite may be equilibrated with several column volumes of a buffer solution of pH 6 to 9 having a phosphate concentration of 8 mM or less, preferably 5 mM or less, and more preferably 2 mM or less (the kind of such buffer solution is not limited, but the following buffer solutions may be used, for example: 5 mM phosphate, 0.2 M sodium chloride, pH 7; 1 mM phosphate, 25 mM TRIS, 0.2 M sodium chloride, pH 7.7; or 2 mM phosphate, 20 mM HEPES, 0.17 M sodium chloride, pH 7). A buffer solution of a denatured product-containing material to be subjected to hydroxyapatite is a buffer solution of pH 6 to 9 having a phosphate concentration of 8 mM or less, preferably 5 mM or less, and more preferably 2 mM or less. After completion of such equilibration, a denatured product-containing material is subjected to the hydroxyapatite. Before elution of soluble thrombomodulin, the hydroxyapatite may be washed with a buffer solution of pH 6 to 9 having a phosphate concentration of 8 mM or less, preferably 5 mM or less, and more preferably 2 mM or less (the kind of such buffer solution is not limited, but the following buffer solutions may be used, for example: 5 mM phosphate, 0.2M sodium chloride, pH 7; 1 mM phosphate, 25 mM TRIS, 0.2M sodium chloride, pH 7.7; or 2 mM phosphate, 20 mM HEPES, 0.17M sodium chloride, pH 7). With regard to the adsorbed denatured product-containing material, soluble thrombomodulin may be separated from a denatured product of the soluble thrombomodulin and they may be then eluted by gradient elution with a phosphate concentration of 0 to 0.5M, using a buffer solution of pH 6 to 9, and preferably of pH 7 to 8. Separation conditions are not particularly limited, as long as they are conditions capable of separating soluble thrombomodulin from a denatured product of the soluble thrombomodulin. Examples of such gradient elution conditions include linear gradient elution conditions and stepwise gradient elution conditions. This gradient elution is preferably carried out with a phosphate concentration of 1 to 40 mM. More preferably, stepwise gradient elution is carried out with a phosphate concentration of 8 to 10 mM, so as to obtain an elution fraction containing soluble thrombomodulin that does not substantially contain a denatured product of the soluble thrombomodulin. By further increasing the concentration of phosphate, a denatured product of soluble thrombomodulin is eluted.

When gradient elution conditions are used, as a method of obtaining an elution fraction containing soluble thrombomodulin that does not substantially contain a denatured product of the soluble thrombomodulin, the same method as that in the case of separating soluble thrombomodulin from a denatured product thereof using an anion exchanger can be applied.

Moreover, soluble thrombomodulin substantially not containing a denatured product thereof can also be obtained as a pass-through fraction by substituting a denatured product-containing material with a suitable buffer solution before subjecting such denatured product-containing material to hydroxyapatite. Such pass-through fraction is a fraction in which soluble thrombomodulin is not adsorbed on the hydroxyapatite when a soluble thrombomodulin-containing material is subjected to the hydroxyapatite. A difference between soluble thrombomodulin and a denatured product thereof in terms of adsorbability on a column is utilized. In this case, as hydroxyapatite, Macro-Prep (R) Ceramic Hydroxyapatite TYPE 1 (BIO-RAD) can be used, for example. A suitable buffer solution used in substitution is a buffer solution of pH 6 to 9 having a phosphate concentration of 5 to 20 mM, and preferably a buffer solution of pH 6 to 7 having a phosphate concentration of 5 to 10 mM. The kind of such buffer solution is not limited. For example, 10 mM phosphate, 10 mM sodium chloride, pH 7 can be used. As a method of obtaining a pass-through fraction, while confirming by an analytic method such as size exclusion chromatography described in Example 7 later that an elution fraction contains soluble thrombomodulin and does not substantially contain a denatured product of the soluble thrombomodulin, such fraction may be appropriately obtained.

Moreover, isocratic elution conditions may also be used. In this case as well, such conditions may be determined, as appropriate, with reference to gradient elution conditions and conditions under which soluble thrombomodulin is eluted from a pass-through fraction.

Preferably, the production method of the present invention does not comprise a step of adjusting the pH of an elution fraction containing soluble thrombomodulin that does not substantially contain a denatured product of the soluble thrombomodulin to pH 4 or less, after a soluble thrombomodulin-containing material has been subjected to an anion exchanger or hydroxyapatite to obtain the aforementioned elution fraction. Moreover, even in the subsequent concentration step and/or desalination step for converting the soluble thrombomodulin to a pharmaceutical material, it is preferable not to adjust the pH of the elution fraction to pH 4 or less.

A preferred example of a method of purifying soluble thrombomodulin from a culture supernatant prepared by culturing cells capable of producing soluble thrombomodulin in a serum component-containing medium or a serum free medium is a purification method using, as an indicator, thrombomodulin activity such as the activity of thrombomodulin to promote protein C activation by thrombin. A specific example is a purification method comprising: roughly purifying a culture supernatant with Q-Sepharose FF used as an ion-exchange column to recover a fraction having thrombomodulin activity; purifying the recovered fraction with a mouse anti-thrombomodulin monoclonal antibody on an affinity column to recover a fraction having high thrombomodulin activity; purifying the recovered fraction with SP-Sepharose FF used as a cation-exchange column; concentrating a pass-through fraction; and then subjecting the resultant fraction to gel filtration to obtain a thrombomodulin active fraction. After completion of such purification with SP-Sepharose FF, the anion exchanger of the present invention, preferably an anion exchanger having a quaternary ammonium group such as SourceQ (GE Healthcare Bio-Sciences), which is a strong anion exchanger, or the hydroxyapatite of the present invention such as Macro-Prep (R) Ceramic Hydroxyapatite TYPE 1 (BIO-RAD), is used under optimal conditions, so as to easily obtain high-purity thrombomodulin that does not substantially contain a denatured product of soluble thrombomodulin.

On the other hand, after purification with a mouse anti-thrombomodulin monoclonal antibody, the anion exchanger of the present invention, preferably an anion exchanger having a quaternary ammonium group such as SourceQ (GE Healthcare Bio-Sciences), which is a strong anion exchanger, is used under optimal conditions, so that a denatured product of soluble thrombomodulin, a mouse antibody-derived product, and in the case of using a serum-containing medium, a serum-derived product can be simultaneously eliminated, thereby easily obtaining high-purity thrombomodulin that does not substantially contain a denatured product of soluble thrombomodulin.

The high-purify thrombomodulin obtained by the aforementioned method is then subjected to a concentration step and/or a desalination step in which the pH is not adjusted to pH 4 or less, so as to obtain a buffer-exchanged, highly purified product. The soluble thrombomodulin obtained by the aforementioned method can be used as a pharmaceutical material.

Further, the present invention provides a method for purifying soluble thrombomodulin in such a way that the soluble thrombomodulin does not substantially contain a denatured product of the soluble thrombomodulin that may be generated from the soluble thrombomodulin under acidic conditions. The present purification method is not particularly limited, as long as it comprises (1) a step of subjecting a soluble thrombomodulin-containing material that contains or is suspected to contain a denatured product of the soluble thrombomodulin to an anion exchanger or hydroxyapatite, and (2) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin. Moreover, as such purification method, a purification method having the characteristic features of the aforementioned method for producing soluble thrombomodulin of the present invention may be applied.

EXAMPLES

The present invention will be more specifically described in the following examples. However, these examples are not intended to limit the scope of the present invention.

Example 1

Rough Purification with Strong Anion-Exchange Column

In accordance with the descriptions of JP Patent Publication (Kokai) No. 11-341990 A (1999), DNA encoding the amino acid sequence shown in SEQ ID NO: 9 was prepared, modified, and then incorporated into Chinese hamster ovary cells by genetic engineering technique. The cells were cultured, and a culture supernatant was then obtained. Thereafter, 41 l of the obtained culture supernatant was filtrated with a 0.2-μm membrane filter (Millipore; Millipak 20). The filtrated culture supernatant was subjected to a Q-Sepharose (GE Healthcare Bio-Sciences) column (diameter: 44 cm; height: 26.3 cm) that had been equilibrated with a 20 mM Tris-HCl buffer solution (pH 7.4) containing 150 mM sodium chloride. Subsequently, the column was washed with 6 column volumes of a 20 mM acetate buffer solution containing 180 mM sodium chloride, and was further washed with 8 column volumes of a 20 mM Tris-HCl buffer solution (pH 7.4) containing 180 mM sodium chloride. Thereafter, elution was initiated with a 20 mM Tris-HCl buffer solution (pH 7.4) containing 300 mM sodium chloride. 0.5 column volumes of an eluate was obtained as a roughly purified product from the initial rise of the peak of the absorbance at 280 nm of the eluate. It is to be noted that the flow rate was set at 760 mL/min.

Example 2

Purification with Monoclonal Antibody

In accordance with the descriptions of JP Patent Publication (Kokai) No. 11-341990 A (1999), an anti-thrombomodulin monoclonal antibody was prepared using human lung-derived thrombomodulin as an antigen. The obtained anti-thrombomodulin monoclonal antibody was then allowed to come into contact with and to react with CNBr-activated Sepharose 4 Fast Flow (GE Healthcare Bio-Sciences), so that the anti-thrombomodulin monoclonal antibody was coupled therewith, thereby producing anti-thrombomodulin monoclonal antibody-bound Sepharose 4 Fast Flow. 16.5 l out of the elution fraction obtained in Example 1 was subjected to a monoclonal antibody column (diameter: 44 cm; height: 10.5 cm) that had been equilibrated with a 20 mM phosphate buffer solution (pH 7.3) containing 0.3 M sodium chloride. The column was washed by supplying 6 column volumes of a 20 mM phosphate buffer solution (pH 7.3) containing 1.0M sodium chloride, and then supplying 3 column volumes of a 0.1M acetate buffer solution (pH 5.0). Thereafter, elution was initiated with a 0.1M glycine-HCl buffer solution (pH 3.0) containing 0.3M sodium chloride. An eluate was obtained from the initial rise to decay of the peak of the absorbance at 280 nm of the eluate. Thereafter, a 0.5M phosphate buffer solution (pH 7.3) was added to the eluate in an amount of 1/10 with respect to the volume of the eluate, so as to obtain a purified solution. It is to be noted that the flow rate was set at 760 mL/min.

Example 3

Purification with Strong Cation-Exchange Column

A 1.0M glycine-HCl buffer solution (pH 2.0) was added to 193 ml out of the purified solution obtained in Example 2, so as to adjust the pH of the solution to pH 3.5. This solution was subjected to a SP-Sepharose FF (GE Healthcare Bio-Sciences) column (diameter: 16 mm; height: 12 cm) that had been equilibrated with a 0.1M glycine buffer solution (pH 3.5) containing 0.3 M NaCl. The column started to be washed with a 100 mM glycine-HCl buffer solution (pH 3.5) containing 300 mM NaCl. A pass-through fraction was obtained from the initial rise to decay of the peak of the absorbance at 280 nm, and it was immediately neutralized with a 0.5M phosphate buffer solution (pH 7.3) so as to adjust the pH of the solution to pH 7, thereby obtaining a highly purified product. It is to be noted that the flow rate was set at 3.3 mL/min. As a result of the measurement by chromatography using the aforementioned Asahipak C4P-50 or the ELISA method described in JP Patent Publication (Kokai) No.

11-341990 A (1999), the content of soluble thrombomodulin in the highly purified product was found to be 99% or more.

Example 4

Separation of Denatured Product of Soluble Thrombomodulin by Anion Exchanger Linear Gradient Elution (1)

10 ml out of the highly purified product obtained in Example 3 was diluted with 30 ml of purified water. 40 ml of the thus diluted solution was subjected to a SourceQ 30 (GE Healthcare Bio-Sciences) column (diameter: 0.5 cm; height: 9.8 cm) that had been equilibrated with a 20 mM phosphate buffer solution (pH 6) containing 0.1M sodium chloride. The column was washed with 3 column volumes of a 20 mM phosphate buffer solution (pH 6), and it started to be eluted by 0.1M to 0.3M sodium chloride linear gradient elution with a 20 mM phosphate buffer solution (pH 6) at an elution volume of 20 column volumes. An eluate was fractionated at a unit of 1 column volume from the initial rise of the peak of the absorbance at 280 nm of the eluate. It is to be noted that the flow rate during the loading of the sample and washing was set at 2.2 mL/min, and that the flow rate during the elution was set at 0.3 mL/min. The chromatogram is shown in FIG. 1.

Example 5

Separation of Denatured Product of Soluble Thrombomodulin by Anion Exchanger Linear Gradient Elution (2)

10 ml out of the highly purified product obtained in Example 3 was diluted with 30 ml of purified water. 40 ml of the thus diluted solution was subjected to a SourceQ 30 (GE Healthcare Bio-Sciences) column (diameter: 0.5 cm; height: 9.8 cm) that had been equilibrated with a 20 mM phosphate buffer solution (pH 7) containing 0.1M sodium chloride. The column was washed with 3 column volumes of a 20 mM phosphate buffer solution (pH 7), and it started to be eluted by 0.1M to 0.3M sodium chloride linear gradient elution with a 20 mM phosphate buffer solution (pH 7) at an elution volume of 20 column volumes. An eluate was fractionated at a unit of 1 column volume from the initial rise of the peak of the absorbance at 280 nm of the eluate. It is to be noted that the flow rate during the loading of the sample and washing was set at 2.2 mL/min, and that the flow rate during the elution was set at 0.3 mL/min. The chromatogram is shown in FIG. 2.

Example 6

Separation of Denatured Product of Soluble Thrombomodulin by Anion Exchanger Linear Gradient Elution (3)

10 ml out of the highly purified product obtained in Example 3 was diluted with 30 ml of purified water. 40 ml of the thus diluted solution was subjected to a SourceQ 30 (GE Healthcare Bio-Sciences) column (diameter: 0.5 cm; height: 9.8 cm) that had been equilibrated with a 20 mM Tris buffer solution (pH 8) containing 0.1M sodium chloride. The column was washed with 3 column volumes of a 20 mM Tris buffer solution (pH 8), and elution was then initiated by 0.1M to 0.3M sodium chloride linear gradient elution with a 20 mM Tris buffer solution (pH 8) at an elution volume of 20 column volumes. An eluate was fractionated at a unit of 1 column volume from the initial rise of the peak of the absorbance at 280 nm of the eluate. It is to be noted that the flow rate during the loading of the sample and washing was set at 2.2 mL/min, and that the flow rate during the elution was set at 0.3 mL/min. The chromatogram is shown in FIG. 3.

Example 7

Evaluation of Contents of Denatured Products of Soluble Thrombomodulins of Examples 4-6

Using an analytical size exclusion chromatography, TSK-GEL G3000SWXL (7.8 mm I.D.×30 cm; TOSOH), the content of a denatured product of soluble thrombomodulin in each fraction was evaluated. The column was equilibrated with a mobile phase. As such mobile phase, a 50 mM phosphate buffer solution (pH 7.3) containing 0.1M sodium sulfate was used. 150 µl of each fraction was subjected to the aforementioned chromatography at a flow rate of 0.9 ml/min, so that it was analyzed. In addition, the recovery rate of each fraction was calculated by measuring the absorbance at 280 nm. The results of Examples 4 to 6 are shown in the following Table 1. Moreover, with regard to the highly purified product obtained in Example 3 as well, the content of a denatured product of soluble thrombomodulin therein was measured by the aforementioned method. As a result, the content was found to be 7.0% (FIG. 4). Under any of the conditions of Examples 4 to 6, a high-purity soluble thrombomodulin that did not substantially contain a denatured product of soluble thrombomodulin could be obtained at a recovery rate of 76% to 81%.

TABLE 1

| | | Fractions 1 to 4 pool | Fraction 5 | Fraction 6 | Fraction 7 |
|---|---|---|---|---|---|
| Example 4 | TM denatured product content rate (%) | 0.0 | 9.3 | 41.5 | 53.8 |
| | Recovery rate (%) | 80 | 9 | 7 | 4 |
| Example 5 | TM denatured product content rate (%) | 0.0 | 3.0 | 35.5 | 54.7 |
| | Recovery rate (%) | 76 | 10 | 8 | 6 |
| Example 6 | TM denatured product content rate (%) | 0.0 | 8.8 | 40.2 | 50.0 |
| | Recovery rate (%) | 81 | 9 | 7 | 3 |

Example 8

Separation of Denatured Product of Soluble Thrombomodulin by Anion Exchanger Stepwise Gradient Elution 70 ml out of the highly purified product obtained in Example 3 was diluted with 210 ml of purified water. The diluted solution was subjected to a SourceQ 30 (GE Healthcare Bio-Sciences) column (diameter: 0.5 cm; height: 20.5 cm) that had been equilibrated with a 20 mM phosphate buffer solution (pH 7.3) containing 30 mM sodium chloride. The column was washed with 3 column volumes of a 20 mM phosphate buffer solution (pH 7.3) containing 30 mM sodium chloride, and elution was started with a 20 mM phosphate buffer solution (pH 7.3) containing 0.18M sodium chloride. An eluate was obtained from the initial rise of the peak of the absorbance at 280 nm of the eluate to 6 column volumes. Using an analytical size exclusion chromatography, TSK-GEL G3000SWXL (TOSOH), the content of a denatured product of soluble thrombomodulin in the eluate was evaluated under the conditions of Example 7. As a result, the content of the denatured product of soluble thrombomodulin was found to be 0.0%. Thus, a high-purity soluble thrombomodulin that did not substantially contain a denatured product of soluble thrombomodulin could be obtained. The recovery rate of the eluate was found to be 89%. It is to be noted that the flow rate during the loading of the sample and washing was set at 0.8 mL/min, and that the flow rate during the elution was set at 0.4 mL/min. The chromatogram is shown in FIG. 5.

Example 9

Obtainment of Soluble Thrombomodulin-Containing Culture Supernatant by Serum Free Culture of Chinese Hamster Ovary Cells, Wherein Human-Derived Thrombomodulin Gene which had been Prepared and Modified was Incorporated by Genetic Engineering Technique As serum free media containing no animal ingredients used in the culture for obtaining a soluble thrombomodulin-containing culture supernatant, two types of media, namely, a medium for seeding and a medium for perfusion culture were prepared.

In order to prepare the medium for seeding, 5 mL of HT supplement (liquid; catalog number: 11067-030; manufacturer: Invitrogen) and 40 mL of 200 mM L-Glutamine (liquid; catalog number: 25030-081; manufacturer: Invitrogen) were aseptically mixed into 1 L of IS CHO-CD (liquid medium; catalog number: 91119-1L; manufacturer: Irvine Scientific). When preserved, the thus prepared medium for seeding was refrigerated (2° C. to 8° C.), and when used, it was heated in a constant temperature bath at 36° C. immediately before use.

In order to prepare the medium for perfusion culture, 20.8 g of IS CHO-CD-A3 (powder medium; catalog number 98688; manufacturer: Irvine Scientific), 2.6 g of common salts (special grade; manufacturer: Wako Pure Chemical Industries, Ltd.), and 4.4 g of sodium bicarbonate (special grade; manufacturer: Wako Pure Chemical Industries, Ltd.) were added to and dissolved in 1 L of deionized ultrafiltrated water, and the mixed solution was then aseptically filtrated with a 0.2-μm filter (made of PVDF; manufacturer: Millipore). The thus prepared medium for perfusion culture was refrigerated (2° C. to 8° C.), when it is preserved and used.

For initiation of seed culture, frozen cells capable of producing soluble thrombomodulin (JP Patent Publication (Kokai) No. 11-341990 A (1999)) were rapidly melted in a 37° C. constant temperature bath, and the cells were then suspended in a medium for seed culture. The suspension was centrifuged (2000 rpm; 2 minutes; Kokusan Chemical Co., Ltd.), and after elimination of a centrifuged supernatant, a cell pellet was suspended in 100 mL of the medium for seed culture. The suspension was dispensed into a 225-cm² T flask culture vessel (manufacturer: BD Biosciences) to start a first step seed culture. The first step seed culture was carried out as static culture in a 36° C., 5% $CO_2$ incubator. When the density of floating living cells in the first step seed culture reached approximately $8 \times 10^5$ cells/mL, the cells were subcultured to a second seed culture.

The second step seed culture and the subsequent cultures were carried out as spinner cultures. The scales and spinner culture vessels used in spinner cultures as seed cultures are as follows: second step seed culture: 400 mL (a spinner flask made of glass; manufacturer: Shibata Scientific Technology Ltd.); third step seed culture: 1.6 L (a spinner flask made of glass; manufacturer: Shibata Scientific Technology Ltd.); and fourth step seed culture: 6 L (a spinner flask made of glass; manufacturer: Shibata Scientific Technology Ltd.). Thus, the cells were successively subcultured, so that the amount of a culture solution was increased. When the density of floating living cells in a seed culture reached approximately $8 \times 10^5$ cells/mL, the cells were subcultured to the next seed culture. In such subculture, a medium for seed culture was added to the previous medium in the sane amount as a value obtained by subtracting the culture scale before subculture from the culture scale after subculture, so as to increase the amount of the culture solution. Spinner culture was carried out in a 36° C., 5% $CO_2$ incubator, using a magnetic stirrer (manufacturer: Shibata Scientific Technology Ltd.) at a stirring number of 60 to 100 rpm.

When the density of floating living cells in the fourth seed culture reached approximately $8 \times 10^5$ cells/mL, 2 L of the seed culture solution was transferred into each of 3 perfusion culture tanks (2-L perfusion culture fermenters; manufacturer: B. E. Marubishi Co., Ltd.), and perfusion culture was then initiated.

In the perfusion culture, quantitative transportation of a perfusion culture medium supplied to a perfusion culture tank was carried out using a perister pump (manufacturer: Master Flex) at a flow rate of 2 L/day.

Cell separation in perfusion culture was carried out using a spin filter established in a perfusion culture tank. The spin filters used in the 3 perfusion culture tanks were of all different types. A first spin filter was a mesh made of stainless steel (FP-10; pore diameter: 10 μm; manufacturer: Fuji Filter MFG Co., Ltd.). A second spin filter was a mesh made of stainless steel (FP-30; pore diameter: 30 μm; manufacturer: Fuji Filter MFG Co., Ltd.). A third spin filter was a mesh made of polyester PETP (pore diameter: 10 μm; catalog number: BB-8808571; manufacturer: Sartorius K. K.), A culture supernatant separated with a spin filter established in a perfusion culture tank was intermittently removed from the tank via the pressure in the culture tank by the action of a level sensor indicating a liquid level of 2 L in the perfusion culture tank, when the amount of the culture solution became 2 L or more. The intermittently removed culture supernatant was transferred into a refrigerated vessel, and it was then refrigerated at 2° C. to 8° C.

Conditions for the perfusion culture were controlled as follows: the temperature in the tank: 35° C. to 37° C.; dissolved oxygen level: 10% to 90%; and pH 6.8 to 7.6.

The perfusion culture was carried out for 30 days. The mean living cell densities during the culture were as follows: the first perfusion culture tank: $17 \times 10^6$ cells/mL; the second perfusion culture tank: $10 \times 10^6$ cells/mL; and the third perfusion culture tank: $18 \times 10^6$ cells/mL.

Culture supernatants obtained from the 3 perfusion culture tanks for a period of time between the $3^{rd}$ day and the $30^{th}$ day of the perfusion culture were gathered, and the mixture was then filtrated with a 0.2-μm filter (made of PVDF; manufacturer: Millipore). The filtrated culture supernatant was refrigerated (2° C. to 8° C.).

Example 10

Purification with Strong Anion-Exchange Column 850 ml out of the culture supernatant obtained in Example 9 was subjected to a Q-Sepharose FF (GE Healthcare Biosciences) column (diameter: 1.6 cm; height: 29 cm) that had been equilibrated with a 20 mM sodium acetate-120 mM acetate buffer solution containing 30 mM sodium chloride. Subsequently, the column was washed with 12 column volumes of a 20 mM sodium acetate-120 mM acetate buffer solution (pH 3.8) containing 30 mM sodium chloride, and elution was then initiated with a 20 mM sodium acetate-40 mM acetate buffer solution (pH 4.2) containing 140 mM sodium chloride. ⅕ column volumes of a 1M HEPES buffer solution (pH 8) containing 10 mM potassium phosphate was added to an eluate from the initial rise of the main peak of the absorbance at 280 nm of the eluate to 2 column volumes, so as to obtain a purified product. It is to be noted that the flow rate was set at 2 mL/min.

Example 11

Separation of Denatured Product of Soluble Thrombomodulin by Hydroxyapatite Stepwise Gradient Elution 20 ml out of the purified product obtained in Example 10 was subjected to a Macro-Prep (R) Ceramic Hydroxyapatite TYPE 1 (BIO-RAD) column (diameter: 0.5 cm; height: 9.7 cm) that had been equilibrated with a 20 mM HEPES buffer solution (pH 7) containing 0.17M sodium chloride and 2 mM sodium phosphate. The column was washed with 6 column volumes of a 20 mM HEPES buffer solution (pH 7) containing 0.17M sodium chloride and 2 mM sodium phosphate, and elution was then carried out with 4 column volumes of a 8 mM phosphate buffer solution (pH 7) containing 10 mM sodium chloride. An eluate was obtained from the initial rise to decay of the peak of the absorbance at 280 nm of the eluate. It is to be noted that the flow rate was set at 0.4 mL/min. Using an analytical size exclusion chromatography, TSK-GEL G3000SWXL (TOSOH), the content of a denatured product of soluble thrombomodulin in the eluate was evaluated under the conditions of Example 7. As a result, the content of the denatured product of soluble thrombomodulin was found to be 0.8% or less. The column was reproduced with a 0.5M phosphate buffer solution (pH 7). The chromatogram is shown in FIG. 6.

Example 12

Rough Purification with Strong Anion-Exchange Column (2)

5.2 l of the culture supernatant obtained in Example 9 was subjected to a Capto Q (GE Healthcare Bio-Sciences) column (diameter: 1.6 cm; height: 26 cm) that had been equilibrated with a 20 mM Tris-HCl buffer solution (pH 7.7) containing 150 mM sodium chloride. Subsequently, the column was washed with 15 column volumes of a 20 mM Tris-HCl buffer solution (pH 7.7) containing 0.18M sodium chloride, and elution was then initiated with a 20 mM Tris-HCl buffer solution (pH 7.7) containing 0.3M sodium chloride. An eluate was obtained from the initial rise of the peak of the absorbance at 280 nm of the eluate to 2 column volumes as a roughly purified product. It is to be noted that the flow rate was set at 10 mL/min.

Example 13

Purification with Monoclonal Antibody (2)

A monoclonal antibody was produced in accordance with Patent Document 2. 72 mL out of the elution fraction obtained in Example 12 was subjected to a monoclonal antibody column (diameter: 5 cm; height: 11 cm) that had been equilibrated with a 20 mM phosphate buffer solution (pH 7.3) containing 0.3M sodium chloride. 6 column volumes of a 20 mM phosphate buffer solution (pH 7.3) containing 1.0M sodium chloride was supplied to the column, and thereafter, 3 column volumes of a 0.1M acetate buffer solution (pH 5.0) was supplied thereto, so that the column was washed. Thereafter, elution was initiated with a 0.1M glycine-HCl buffer solution (pH 3.0) containing 20 mM sodium chloride, so as to obtain an eluate from the initial rise to decay of the peak of the absorbance at 280 nm of the eluate. Thereafter, 15% by volume of a 0.3 M phosphate buffer solution (pH 7.3) was added to the eluate, so as to obtain a purified solution. It is to be noted that the flow rate was set at 9.8 mL/min. As a result of the measurement by chromatography using the aforementioned Asahipak C4P-50 or the ELISA method described in JP Patent Publication (Kokai) No. 11-341990 A (1999), the content of soluble thrombomodulin in the highly purified solution was found to be 99% or more.

Example 14

High Purification and Elimination of Denatured Product of Soluble Thrombomodulin with Strong Anion Exchanger 75 mL out of the purified solution obtained in Example 13 was subjected to a SourceQ 30 (GE Healthcare Bio-Sciences) column (diameter: 0.5 cm; height: 20.5 cm) that had been equilibrated with a 0.1M acetate buffer solution (pH 4) containing 40 mM sodium chloride. 2 column volumes of a 0.1M acetate buffer solution (pH 4) containing 40 mM sodium chloride was supplied to the column, then 4 column volumes of a 0.1M acetate buffer solution (pH 4) containing 50 mM sodium chloride was supplied thereto, and thereafter, 3 column volumes of a 20 mM phosphate buffer solution (pH 7.3) containing 30 mM sodium chloride was supplied thereto, so that the column was washed. Thereafter, elution was initiated with a 20 mM phosphate buffer solution (pH 7.3) containing 0.18M sodium chloride, so as to obtain an eluate from the initial rise of the peak of the absorbance at 280 nm of the eluate to 6 column volumes thereof. It is to be noted that the flow rate during the loading of the sample was set at 1 mL/min, and that the flow rate during washing and elution was set at 0.3 mL/min. Using an analytical size exclusion chromatography, TSK-GEL G3000SWXL (TOSOH), the content of a denatured product of soluble thrombomodulin in the eluate was evaluated under the conditions of Example 7. As a result, the content of the denatured product of soluble thrombomodulin was found to be 0.1%. Thus, a high-purity soluble thrombomodulin that did not substantially contain a denatured product of soluble thrombomodulin was obtained. The recovery rate of the eluate was found to be 71%. The chromatogram is shown in FIG. 7.

Example 15

Evaluation of Amount of Proteins in which Different Types of Products (Mouse Antibody-Derived Product and Chinese Hamster Ovary Cell-Derived Product) are Mixed By the ELISA method described in JP Patent Publication (Kokai) No. 11-341990 A (1999), the elution fractions of Examples 13 and 14 were evaluated. The absorbance at 280 nm of each elution fraction was measured. The results obtained by evaluating such elution fraction based on the mixed amount per absorbance are shown in the following Table 2. The mixed amounts of ingredients could be simultaneously decreased.

TABLE 2

| | Mouse antibody-derived product (ng/OD) | Chinese hamster ovary cell-derived product (ng/OD) |
|---|---|---|
| Example 13 | 1 | 102 |
| Example 14 | N.D. | N.D. |

SEQUENCE LISTING

Figure 1:
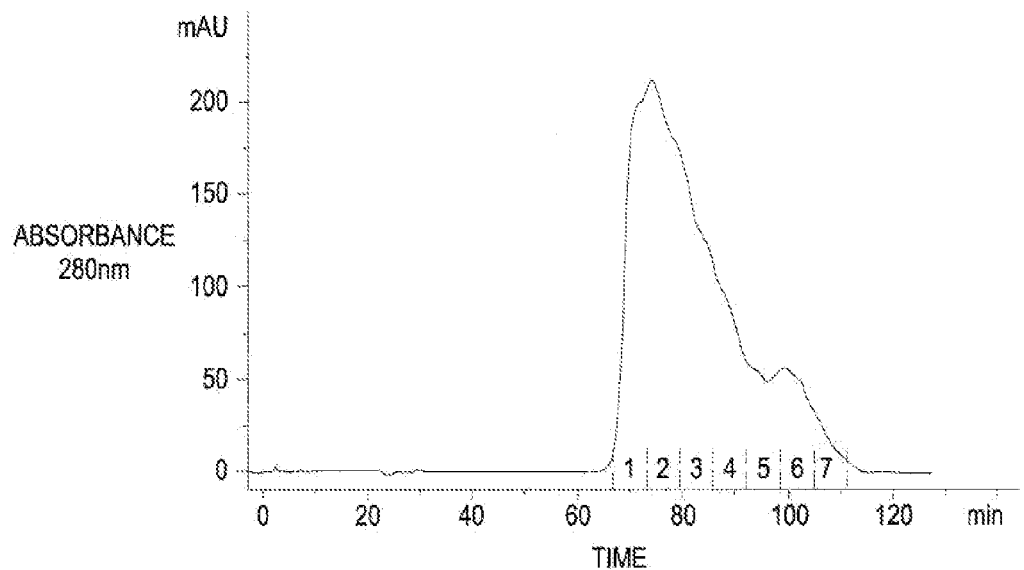
FIG. 1 shows a chromatogram in separation of a denatured product of soluble thrombomodulin by the anion exchanger linear gradient elution in Example 4.
Figure 2:
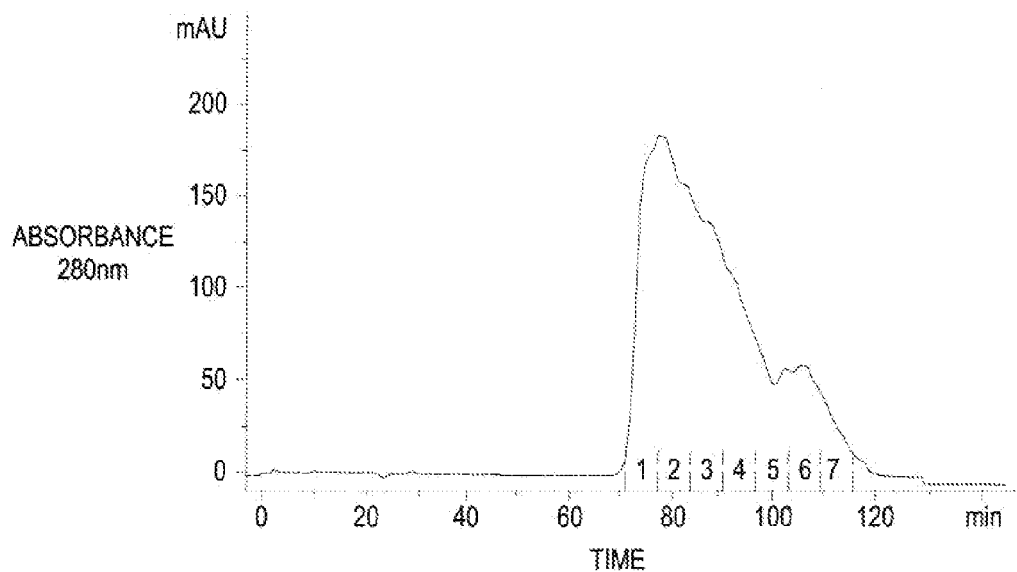
FIG. 2 shows a chromatogram in separation of a denatured product of soluble thrombomodulin by anion exchanger linear gradient elution in Example 5.
Figure 3:
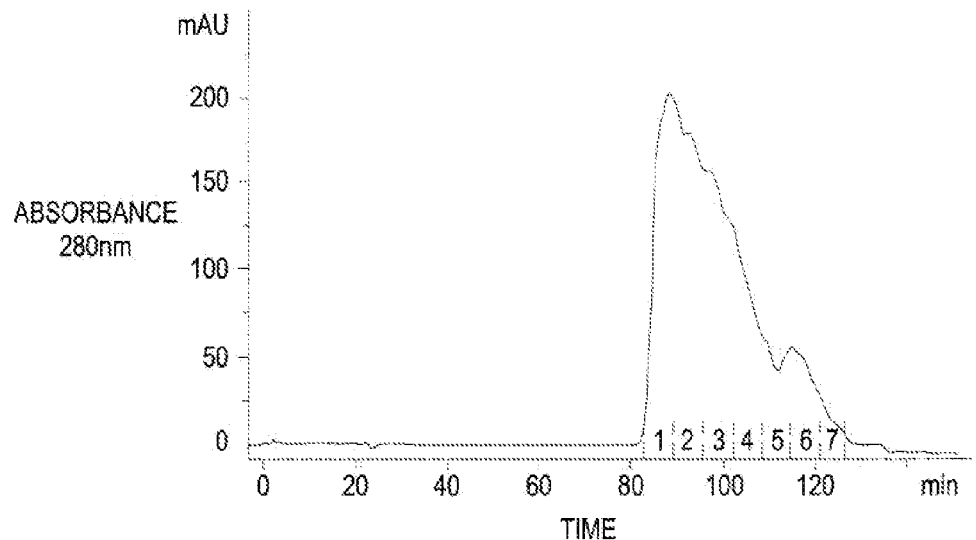
FIG. 3 shows a chromatogram in separation of a denatured product of soluble thrombomodulin by the anion exchanger linear gradient elution in Example 6.
Figure 4:
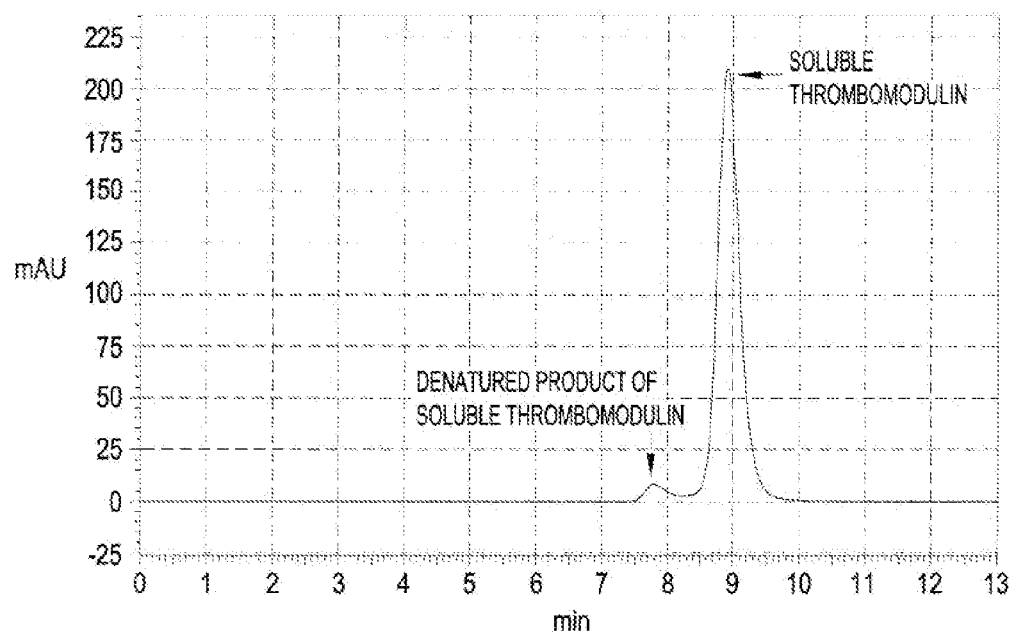
FIG. 4 shows the results obtained by measuring the content of a denatured product of soluble thrombomodulin in the highly purified product obtained in Example 3.
Figure 5:
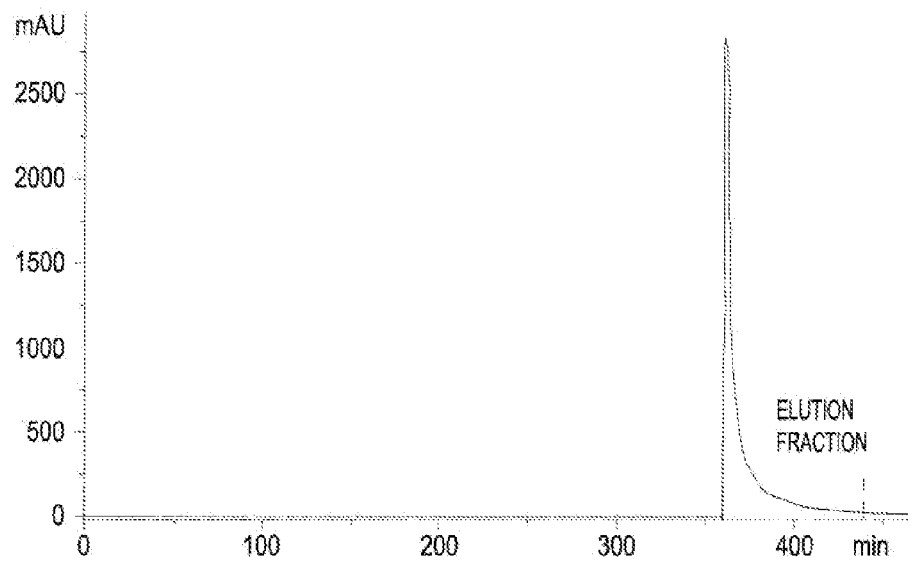
FIG. 5 shows a chromatogram in elimination of a denatured product of soluble thrombomodulin by the anion exchanger stepwise gradient elution in Example 8.
Figure 6:
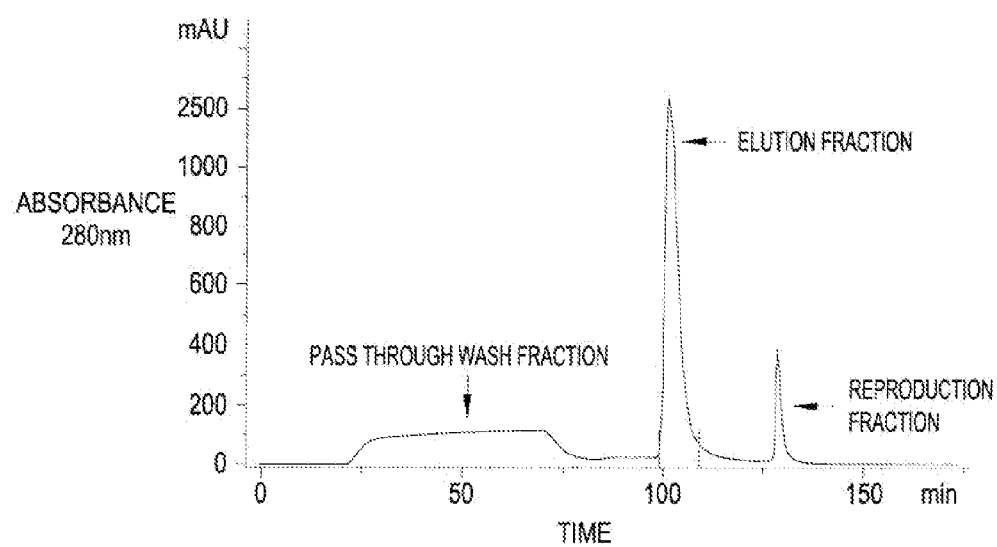
FIG. 6 shows a chromatogram in elimination of a denatured product of soluble thrombomodulin by the hydroxyapatite stepwise gradient elution in Example 11.
Figure 7:
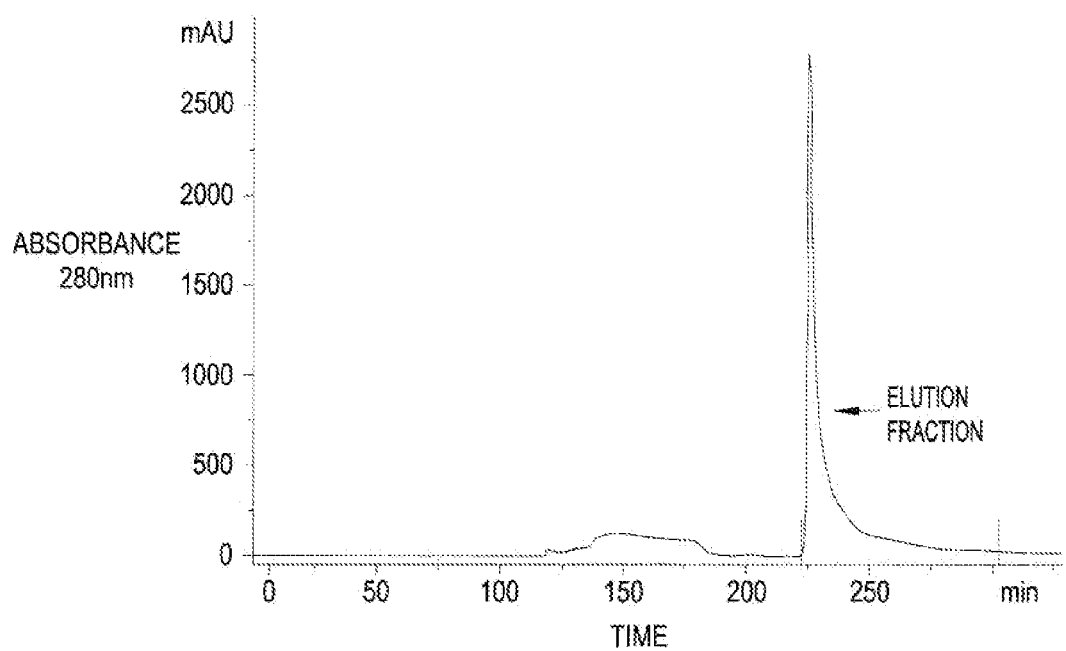
FIG. 7 shows a chromatogram in high purification and elimination of a denatured product of soluble thrombomodulin with a strong anion exchanger in Example 14.

```
<160> NUMBER OF SEQ ID NOS: 13

<210> SEQ ID NO 1
<211> LENGTH: 132
<212> TYPE: PRT
<213> ORGANISM: human

<400> SEQUENCE: 1

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
            20                  25                  30

Leu Asn Gln Thr Ser Tyr Leu Cys Val Cys Ala Glu Gly Phe Ala Pro
        35                  40                  45

Ile Pro His Glu Pro His Arg Cys Gln Met Phe Cys Asn Gln Thr Ala
    50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
            100                 105                 110

Thr Phe Glu Cys Ile Cys Gly Pro Asp Ser Ala Leu Val Arg His Ile
        115                 120                 125

Gly Thr Asp Cys
    130

<210> SEQ ID NO 2
<211> LENGTH: 396
<212> TYPE: DNA
<213> ORGANISM: human

<400> SEQUENCE: 2
atgcttgggg tcctggtcct tggcgcgctg gccctggccg gctgggggtt ccccgacccg      60
tgcttcagag ccaactgcga gtaccagtgc cagcccctga accaaactag ctacctctgc     120
gtctgcgccg agggcttcgc gcccattccc acgagccgc acaggtgcca gatgttttgc      180
aaccagactg cctgtccagc cgactgcgac cccaacaccc aggctagctg tgagtgccct     240
gaaggctaca tcctggacga cggtttcatc tgcacggaca tcgacgagtg cgaaaacggc     300
ggcttctgct ccggggtgtg ccacaacctc cccggtacct cgagtgcat ctgcgggccc      360 gactcggccc ttgtccgcca cattggcacc gactgt                              396
```

<210> SEQ ID NO 3
<211> LENGTH: 132
<212> TYPE: PRT
<213> ORGANISM: human

<400> SEQUENCE: 3

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
            20                  25                  30

Leu Asn Gln Thr Ser Tyr Leu Cys Val Cys Ala Glu Gly Phe Ala Pro
        35                  40                  45

Ile Pro His Glu Pro His Arg Cys Gln Met Phe Cys Asn Gln Thr Ala
    50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
            100                 105                 110

Thr Phe Glu Cys Ile Cys Gly Pro Asp Ser Ala Leu Ala Arg His Ile
        115                 120                 125

Gly Thr Asp Cys
    130

<210> SEQ ID NO 4
<211> LENGTH: 396
<212> TYPE: DNA
<213> ORGANISM: human

<400> SEQUENCE: 4
atgcttgggg tcctggtcct tggcgcgctg gccctggccg gcctgggggtt ccccgacccg        60 tgcttcagag ccaactgcga gtaccagtgc cagcccctga accaaactag ctacctctgc       120
gtctgcgccg agggcttcgc gcccattccc cacgagccgc acaggtgcca gatgttttgc       180
aaccagactg cctgtccagc cgactgcgac cccaacaccc aggctagctg tgagtgccct       240
gaaggctaca tcctggacga cggtttcatc tgcacggaca tcgacgagtg cgaaaacggc       300
ggcttctgct ccggggtgtg ccacaacctc cccggtacct tcgagtgcat ctgcgggccc       360
gactcggccc ttgcccgcca cattggcacc gactgt                                 396

<210> SEQ ID NO 5
<211> LENGTH: 480
<212> TYPE: PRT
<213> ORGANISM: human

<400> SEQUENCE: 5

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

-continued

```
Ser Val Ala Ala Asp Val Ile Ser Leu Leu Leu Asn Gly Asp Gly Gly
 65                  70                  75                  80

Val Gly Arg Arg Arg Leu Trp Ile Gly Leu Gln Leu Pro Pro Gly Cys
                 85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
        370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
            450                 455                 460

Ile Cys Gly Pro Asp Ser Ala Leu Val Arg His Ile Gly Thr Asp Cys
465                 470                 475                 480
```

<210> SEQ ID NO 6
<211> LENGTH: 1440
<212> TYPE: DNA
<213> ORGANISM: human

<400> SEQUENCE: 6

| | | | | | |
|---|---|---|---|---|---|
| atgcttgggg | tcctggtcct | tggcgcgctg | gccctggccg | gctgggggtt | ccccgcaccc | 60 |
| gcagagccgc | agccgggtgg | cagccagtgc | gtcgagcacg | actgcttcgc | gctctacccg | 120 |
| ggccccgcga | ccttcctcaa | tgccagtcag | atctgcgacg | gactgcgggg | ccacctaatg | 180 |
| acagtgcgct | cctcggtggc | tgccgatgtc | atttccttgc | tactgaacgg | cgacggcggc | 240 |
| gttggccgcc | ggcgcctctg | gatcggcctg | cagctgccac | ccggctgcgg | cgaccccaag | 300 |
| cgcctcgggc | ccctgcgcgg | cttccagtgg | gttacgggag | acaacaacac | cagctatagc | 360 |
| aggtgggcac | ggctcgacct | caatggggct | ccctctgcg | gccgttgtg | cgtcgctgtc | 420 |
| tccgctgctg | aggccactgt | gcccagcgag | ccgatctggg | aggagcagca | gtgcgaagtg | 480 |
| aaggccgatg | cttcctctg | cgagttccac | ttcccagcca | cctgcaggcc | actggctgtg | 540 |
| gagcccggcg | ccgcggctgc | cgccgtctcg | atcacctacg | gcaccccgtt | cgcggcccgc | 600 |
| ggagcggact | ccaggcgct | gccggtgggc | agctccgccg | cggtggctcc | cctcggctta | 660 |
| cagctaatgt | gcaccgcgcc | gccggagcg | gtccaggggc | actgggccag | ggaggcgccg | 720 |
| ggcgcttggg | actgcagcgt | ggagaacggc | ggctgcgagc | acgcgtgcaa | tgcgatccct | 780 |
| ggggctcccc | gctgccagtg | cccagccggc | gccgccctgc | aggcagacgg | cgcgctcctgc | 840 |
| accgcatccg | cgacgcagtc | ctgcaacgac | ctctgcgagc | acttctgcgt | tcccaacccc | 900 |
| gaccagccgg | gctcctactc | gtgcatgtgc | gagaccggct | accggctggc | ggccgaccaa | 960 |
| caccggtgcg | aggacgtgga | tgactgcata | ctggagccca | gtccgtgtcc | gcagcgctgt | 1020 |
| gtcaacacac | agggtggctt | cgagtgccac | tgctaccct | actacgacct | ggtggacggc | 1080 |
| gagtgtgtgg | agcccgtgga | cccgtgcttc | agagccaact | gcgagtacca | gtgccagccc | 1140 |
| ctgaaccaaa | ctagctacct | ctgcgtctgc | gccgagggct | tcgcgcccat | tccccacgag | 1200 |
| ccgcacaggt | gccagatgtt | ttgcaaccag | actgcctgtc | agccgactg | cgaccccaac | 1260 |
| acccaggcta | gctgtgagtg | ccctgaaggc | tacatcctgg | acgacggttt | catctgcacg | 1320 |
| gacatcgacg | agtgcgaaaa | cggcggcttc | tgctccgggg | tgtgccacaa | cctccccggt | 1380 |
| accttcgagt | gcatctgcgg | gcccgactcg | gcccttgtcc | gccacattgg | caccgactgt | 1440 |

<210> SEQ ID NO 7
<211> LENGTH: 480
<212> TYPE: PRT
<213> ORGANISM: human

<400> SEQUENCE: 7

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
            85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
            130                 135                 140

Ala Thr Val Pro Ser Glu Pro Ile Trp Glu Glu Gln Cys Glu Val
145                 150                 155                 160

Lys Ala Asp Gly Phe Leu Cys Glu Phe His Phe Pro Ala Thr Cys Arg
                    165                 170                 175

Pro Leu Ala Val Glu Pro Gly Ala Ala Ala Ala Val Ser Ile Thr
                    180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
            210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                    245                 250                 255

Asn Ala Ile Pro Gly Ala Pro Arg Cys Gln Cys Pro Ala Gly Ala Ala
                    260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
            290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                    325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
            370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                    405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
            450                 455                 460

Ile Cys Gly Pro Asp Ser Ala Leu Ala Arg His Ile Gly Thr Asp Cys
465                 470                 475                 480

<210> SEQ ID NO 8
<211> LENGTH: 1440
<212> TYPE: DNA

<213> ORGANISM: human

<400> SEQUENCE: 8

```
atgcttgggg tcctggtcct tggcgcgctg ccctggccg gctgggggtt ccccgcaccc      60
gcagagccgc agccgggtgg cagccagtgc gtcgagcacg actgcttcgc gctctacccg    120
ggccccgcga ccttcctcaa tgccagtcag atctgcgacg gactgcgggg ccacctaatg    180
acagtgcgct cctcggtggc tgccgatgtc atttccttgc tactgaacgg cgacggcggc    240
gttggccgcc ggcgcctctg gatcggcctg cagctgccac ccggctgcgg cgaccccaag    300
cgcctcgggc cctgcgcgg cttccagtgg gttacgggag acaacaacac cagctatagc    360
aggtgggcac ggctcgacct caatggggct cccctctgcg gcccgttgtg cgtcgctgtc    420
tccgctgctg aggccactgt gcccagcgag ccgatctggg aggagcagca gtgcgaagtg    480
aaggccgatg gcttcctctg cgagttccac ttcccagcca cctgcaggcc actggctgtg    540
gagcccggcg ccgcggctgc cgccgtctcg atcacctacg caccccgtt cgcggcccgc    600
ggagcggact tccaggcgct gccggtgggc agctccgccg cggtggctcc cctcggctta    660
cagctaatgt gcaccgcgcc gcccggagcg gtccaggggc actgggccag ggaggcgccg    720
ggcgcttggg actgcagcgt ggagaacggc ggctgcgagc acgcgtgcaa tgcgatccct    780
ggggctcccc gctgccagtg cccagccggc gccgccctgc aggcagacgg cgctcctgc    840
accgcatccg cgacgcagtc ctgcaacgac ctctgcgagc acttctgcgt tcccaacccc    900
gaccagccgg gctcctactc gtgcatgtgc gagaccggct accggctggc ggccgaccaa    960
caccggtgcg aggacgtgga tgactgcata ctggagccca gtccgtgtcc gcagcgctgt   1020
gtcaacacac agggtggctt cgagtgccac tgctaccctc actacgacct ggtggacggc   1080
gagtgtgtgg agcccgtgga cccgtgcttc agagccaact gcgagtacca gtgccagccc   1140
ctgaaccaaa ctagctacct ctgcgtctgc gccgagggct cgcgcccat tccccacgag   1200
ccgcacaggt gccagatgtt ttgcaaccag actgcctgtc cagccgactg cgaccccaac   1260
acccaggcta gctgtgagtg ccctgaaggc tacatcctgg acgacggttt catctgcacg   1320
gacatcgacg agtgcgaaaa cggcggcttc tgctccgggg tgtgccacaa cctccccggt   1380
accttcgagt gcatctgcgg gccgactcg gcccttgccc gccacattgg caccgactgt   1440
```

<210> SEQ ID NO 9
<211> LENGTH: 516
<212> TYPE: PRT
<213> ORGANISM: human

<400> SEQUENCE: 9

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95
```

```
Gly Asp Pro Lys Arg Leu Gly Pro Leu Arg Gly Phe Gln Trp Val Thr
                100                 105                 110
Gly Asp Asn Asn Thr Ser Tyr Ser Arg Trp Ala Arg Leu Asp Leu Asn
            115                 120                 125
Gly Ala Pro Leu Cys Gly Pro Leu Cys Val Ala Val Ser Ala Ala Glu
        130                 135                 140
Ala Thr Val Pro Ser Glu Pro Ile Trp Glu Glu Gln Gln Cys Glu Val
145                 150                 155                 160
Lys Ala Asp Gly Phe Leu Cys Glu Phe His Phe Pro Ala Thr Cys Arg
                165                 170                 175
Pro Leu Ala Val Glu Pro Gly Ala Ala Ala Ala Val Ser Ile Thr
            180                 185                 190
Tyr Gly Thr Pro Phe Ala Ala Arg Gly Ala Asp Phe Gln Ala Leu Pro
        195                 200                 205
Val Gly Ser Ser Ala Ala Val Ala Pro Leu Gly Leu Gln Leu Met Cys
    210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Gly Cys Glu His Ala Cys
                245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
        275                 280                 285
Asn Asp Leu Cys Glu His Phe Cys Val Pro Asn Pro Asp Gln Pro Gly
    290                 295                 300
Ser Tyr Ser Cys Met Cys Glu Thr Gly Tyr Arg Leu Ala Ala Asp Gln
305                 310                 315                 320
His Arg Cys Glu Asp Val Asp Cys Ile Leu Glu Pro Ser Pro Cys
                325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
        355                 360                 365
Cys Phe Arg Ala Asn Cys Glu Tyr Gln Cys Gln Pro Leu Asn Gln Thr
    370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
        435                 440                 445
Gly Phe Cys Ser Gly Val Cys His Asn Leu Pro Gly Thr Phe Glu Cys
    450                 455                 460
Ile Cys Gly Pro Asp Ser Ala Leu Val Arg His Ile Gly Thr Asp Cys
465                 470                 475                 480
Asp Ser Gly Lys Val Asp Gly Gly Asp Ser Gly Ser Gly Glu Pro Pro
                485                 490                 495
Pro Ser Pro Thr Pro Gly Ser Thr Leu Thr Pro Pro Ala Val Gly Leu
            500                 505                 510
```

Val His Ser Gly
        515

<210> SEQ ID NO 10
<211> LENGTH: 1548
<212> TYPE: DNA
<213> ORGANISM: human

<400> SEQUENCE: 10

```
atgcttgggg tcctggtcct tggcgcgctg gccctggccg gcctggggtt ccccgcaccc      60
gcagagccgc agccgggtgg cagccagtgc gtcgagcacg actgcttcgc gctctacccg     120
ggccccgcga ccttcctcaa tgccagtcag atctgcgacg actgcggggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc ccctgcgcgg cttccagtgg gttacgggag acaacaacac cagctatagc     360
aggtgggcac ggctcgacct caatggggct ccctctgcg gcccgttgtg cgtcgctgtc      420
tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg caccccgtt cgcggcccgc      600
ggagcggact ccaggcgct gccggtgggc agctccgccg cggtggctcc cctcggctta     660
cagctaatgt gcaccgcgcc gcccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc ccgccctgc aggcagacgg cgctcctgc      840
accgcatccg cgacgcagtc ctgcaacgac ctctgcgagc acttctgcgt tcccaacccc     900
gaccagccgg gctcctactc gtgcatgtgc gagaccggct accggctggc ggccgaccaa     960
caccggtgcg aggacgtgga tgactgcata ctggagccca gtccgtgtcc gcagcgctgt    1020
gtcaacacac agggtggctt cgagtgccac tgctaccctc tactacgacct ggtggacggc    1080
gagtgtgtgg agcccgtgga cccgtgcttc agagccaact gcgagtacca gtgccagccc    1140
ctgaaccaaa ctagctacct ctgcgtctgc gccgagggct cgcgcccat tcccacgag     1200
ccgcacaggt gccagatgtt ttgcaaccag actgcctgtc agccgactg cgaccccaac    1260
acccaggcta gctgtgagtg ccctgaaggc tacatcctgg acgacggttt catctgcacg    1320
gacatcgacg agtgcgaaaa cggcggcttc tgctccgggg tgtgccacaa cctccccggt    1380
accttcgagt gcatctgcgg gcccgactcg gcccttgtcc gccacattgg caccgactgt    1440
gactccggca aggtggacgg tggcgacagc ggctctggcg agcccccgcc cagcccgacg    1500
cccggctcca ccttgactcc tccggccgtg gggctcgtgc attcgggc              1548
```

<210> SEQ ID NO 11
<211> LENGTH: 516
<212> TYPE: PRT
<213> ORGANISM: human

<400> SEQUENCE: 11

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

```
Ser Gln Ile Cys Asp Gly Leu Arg Gly His Leu Met Thr Val Arg Ser
    50                  55                  60
Ser Val Ala Ala Asp Val Ile Ser Leu Leu Leu Asn Gly Asp Gly Gly
65                  70                  75                  80
Val Gly Arg Arg Arg Leu Trp Ile Gly Leu Gln Leu Pro Pro Gly Cys
                85                  90                  95
Gly Asp Pro Lys Arg Leu Gly Pro Leu Arg Gly Phe Gln Trp Val Thr
            100                 105                 110
Gly Asp Asn Asn Thr Ser Tyr Ser Arg Trp Ala Arg Leu Asp Leu Asn
            115                 120                 125
Gly Ala Pro Leu Cys Gly Pro Leu Cys Val Ala Val Ser Ala Ala Glu
            130                 135                 140
Ala Thr Val Pro Ser Glu Pro Ile Trp Glu Glu Gln Gln Cys Glu Val
145                 150                 155                 160
Lys Ala Asp Gly Phe Leu Cys Glu Phe His Phe Pro Ala Thr Cys Arg
                165                 170                 175
Pro Leu Ala Val Glu Pro Gly Ala Ala Ala Ala Val Ser Ile Thr
                180                 185                 190
Tyr Gly Thr Pro Phe Ala Ala Arg Gly Ala Asp Phe Gln Ala Leu Pro
            195                 200                 205
Val Gly Ser Ser Ala Ala Val Ala Pro Leu Gly Leu Gln Leu Met Cys
            210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Cys Glu His Ala Cys
                245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
            275                 280                 285
Asn Asp Leu Cys Glu His Phe Cys Val Pro Asn Pro Asp Gln Pro Gly
            290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
            355                 360                 365
Cys Phe Arg Ala Asn Cys Glu Tyr Gln Cys Gln Pro Leu Asn Gln Thr
            370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
            435                 440                 445
Gly Phe Cys Ser Gly Val Cys His Asn Leu Pro Gly Thr Phe Glu Cys
            450                 455                 460
```

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly
        515

<210> SEQ ID NO 12
<211> LENGTH: 1548
<212> TYPE: DNA
<213> ORGANISM: human

<400> SEQUENCE: 12

| | | |
|---|---|---|
| atgcttgggg tcctggtcct tggcgcgctg gccctggccg gcctggggtt ccccgcaccc | 60 |
| gcagagccgc agccgggtgg cagccagtgc gtcgagcacg actgcttcgc gctctacccg | 120 |
| ggccccgcga ccttcctcaa tgccagtcag atctgcgacg gactgcgggg ccacctaatg | 180 |
| acagtgcgct cctcggtggc tgccgatgtc atttccttgc tactgaacgg cgacggcggc | 240 |
| gttggccgcc ggcgcctctg gatcggcctg cagctgccac ccggctgcgg cgaccccaag | 300 |
| cgcctcgggc cctgcgcgg cttccagtgg gttacgggag acaacaacac cagctatagc | 360 |
| aggtgggcac ggctcgacct caatgggct ccccctctgcg gcccgttgtg cgtcgctgtc | 420 |
| tccgctgctg aggccactgt gcccagcgag ccgatctggg aggagcagca gtgcgaagtg | 480 |
| aaggccgatg gcttcctctg cgagttccac ttcccagcca cctgcaggcc actggctgtg | 540 |
| gagcccggcg ccgcggctgc cgccgtctcg atcacctacg caccccgtt cgcggcccgc | 600 |
| ggagcggact ccaggcgct gccggtgggc agctccgccg cggtggctcc cctcggctta | 660 |
| cagctaatgt gcaccgcgcc gcccggagcg gtccaggggc actgggccag ggaggcgccg | 720 |
| ggcgcttggg actgcagcgt ggagaacggc ggctgcgagc acgcgtgcaa tgcgatccct | 780 |
| ggggctcccc gctgccagtg cccagccggc gccgccctgc aggcagacgg cgcgctcctgc | 840 |
| accgcatccg cgacgcagtc ctgcaacgac ctctgcgagc acttctgcgt tcccaacccc | 900 |
| gaccagccgg gctcctactc gtgcatgtgc gagaccggct accggctggc ggccgaccaa | 960 |
| caccggtgcg aggacgtgga tgactgcata ctggagccca gtccgtgtcc gcagcgctgt | 1020 |
| gtcaacacac agggtggctt cgagtgccac tgctacccta actacgacct ggtggacggc | 1080 |
| gagtgtgtgg agcccgtgga cccgtgcttc agagccaact gcgagtacca gtgccagccc | 1140 |
| ctgaaccaaa ctagctacct ctgcgtctgc gccgagggct cgcgcccat tccccacgag | 1200 |
| ccgcacaggt gccagatgtt ttgcaaccag actgcctgtc cagccgactg cgaccccaac | 1260 |
| acccaggcta gctgtgagtg ccctgaaggc tacatcctgg acgacggttt catctgcacg | 1320 |
| gacatcgacg agtgcgaaaa cggcggcttc tgctccgggg tgtgccacaa cctccccggt | 1380 |
| accttcgagt gcatctgcgg gccccgactcg gcccttgccc gccacattgg caccgactgt | 1440 |
| gactccggca aggtggacgg tggcgacagc ggctctggcg agccccgcc cagcccgacg | 1500 |
| cccggctcca ccttgactcc tccggccgtg gggctcgtgc attcgggc | 1548 |

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic

```
    DNA

<400> SEQUENCE: 13
aatgtggcgg gcaagggccg a                                             21
```

The invention claimed is:

1. A method for producing soluble thrombomodulin substantially not containing a denatured product of the soluble thrombomodulin that may be generated from the soluble thrombomodulin under acidic conditions, which comprises:
   (1) a step of leaving the soluble thrombomodulin under acidic conditions of pH 5 or less;
   (2) a step of subjecting a soluble thrombomodulin-containing material that contains or is suspected to contain a denatured product of the soluble thrombomodulin, which is obtained by step (1), to an anion exchanger or hydroxyapatite; and
   (3) a step of obtaining a soluble thrombomodulin-containing fraction that does not substantially contain a denatured product of the soluble thrombomodulin under separation conditions in which the soluble thrombomodulin can be separated from a denatured product of the soluble thrombomodulin, wherein the anion exchanger comprises a buffer solution of pH 5 to 9, and wherein the hydroxyapatite comprises a buffer solution of pH 6 to 9,
   wherein the content of the denatured product of the soluble thrombomodulin in the soluble thrombomodulin that does not substantially contain the denatured product of soluble thrombomodulin is 3% or less.

2. The production method according to claim 1, wherein the step (1) is a step of leaving the soluble thrombomodulin under acidic conditions of pH 4 or less.

3. The production method according to claim 1, wherein the step (2) is a step of subjecting the soluble thrombomodulin-containing material that contains or is suspected to contain a denatured product of the soluble thrombomodulin, which is obtained by step (1), to the anion exchanger.

4. The production method according to claim 1, wherein the step (2) is a step of subjecting the soluble thrombomodulin-containing material that contains or is suspected to contain a denatured product of the soluble thrombomodulin, which is obtained by step (1), to the hydroxyapatite.

5. The production method according to claim 1, wherein the content of the soluble thrombomodulin is 80% or more with respect to total proteins in the soluble thrombomodulin-containing material.

6. The production method according to claim 1, wherein the step (3) is a step of carrying out linear gradient elution, stepwise gradient elution, or gradient elution in which linear gradient elution is combined with stepwise gradient elution, so as to obtain an elution fraction containing soluble thrombomodulin that does not substantially contain a denatured product of the soluble thrombomodulin.

7. The production method according to claim 1, wherein the step (3) is a step of obtaining a pass-through fraction, in which a fraction containing soluble thrombomodulin that does not substantially contain a denatured product of the soluble thrombomodulin is obtained.

8. The production method according to claim 1, wherein the step (3) is a step of carrying out isocratic elution to obtain an elution fraction containing soluble thrombomodulin that does not substantially contain a denatured product of the soluble thrombomodulin.

9. The production method according to claim 1, wherein the step (2) is a step of subjecting the soluble thrombomodulin-containing material to an anion exchanger comprising a buffer solution of pH 4 to 9; and the step (3) is a step of carrying out linear gradient elution, stepwise gradient elution, or gradient elution in which linear gradient elution is combined with stepwise gradient elution, comprising a buffer solution of pH 5 to 9 having a salt concentration of 0 to 1 M, to obtain an elution fraction containing soluble thrombomodulin that does not substantially contain a denatured product of the soluble thrombomodulin, either (a) after the position of a fraction from which the soluble thrombomodulin is eluted has previously been confirmed, or (b) while confirming the presence of the soluble thrombomodulin in the elution fraction.

10. The production method according to claim 1, wherein the step (2) is a step of subjecting the soluble thrombomodulin-containing material to an anion exchanger comprising a buffer solution of pH 5 to 8 having a salt concentration of 0.1 to 0.2 M and the step (3 is a step of obtaining a pass-through fraction comprising a buffer solution of pH 5 to 8 having a salt concentration of 0.1 to 0.2 M, to obtain a fraction containing soluble thrombomodulin that does not substantially contain a denatured product of the soluble thrombomodulin.

11. The production method according to claim 1, wherein the step (2) is a step of subjecting the soluble thrombomodulin-containing material to hydroxyapatite comprising a buffer solution of pH 6 to 9 having a phosphate concentration of 8 mM or less; and the step (3) is a step of carrying out linear gradient elution, stepwise gradient elution, or gradient elution in which linear gradient elution is combined with stepwise gradient elution, comprising a buffer solution of pH 6 to 9 having a phosphate concentration of 0 to 0.5 M, to obtain an elution fraction containing soluble thrombomodulin that does not substantially contain a denatured product of the soluble thrombomodulin, either (a) after the position of a fraction from which the soluble thrombomodulin is eluted has previously been confirmed, or (b) while confirming the presence of the soluble thrombomodulin in the elution fraction.

12. The production method according to claim 1, wherein the step (2) is a step of subjecting the soluble thrombomodulin-containing material to hydroxyapatite comprising a buffer solution of pH 6 to 9 having a Phosphate concentration of 5 to 20 mM or less; and the step (3) is a step of obtaining a pass-through fraction using a buffer solution of pH 6 to 9 having a phosphate concentration of 5 to 20 mM, to obtain a fraction containing soluble thrombomodulin that does not substantially contain a denatured product of the soluble thrombomodulin.

13. The production method according to any one of claims 1 to 12, which does not comprise a step of adjusting the pH of an elution fraction containing soluble thrombomodulin that does not substantially contain a denatured product of the soluble thrombomodulin to pH 4 or less, after the elation fraction has been obtained.

14. The production method according to any one of claims 1 to 12, which is a production method comprising a concentration step and/or a desalination step, wherein the pH of an elution fraction containing soluble thrombomodulin that does not substantially contain a denatured product of the soluble thrombomodulin is not adjusted to pH 4 or less after the elution fraction has been obtained, and wherein the production method is used to convert the soluble thrombomodulin to a pharmaceutical material.

15. The production method according to claim 1, wherein the content of the denatured product of the soluble thrombomodulin in the soluble thrombomodulin that does not substantially contain the denatured product of soluble thrombomodulin is 1% or less.

16. The production method according to any one of claims 1 to 12, wherein the soluble thrombomodulin is thrombomodulin obtained from transformant cells prepared by transfecting host cells with DNA encoding the amino acid sequence as set forth in SEQ ID NO: 9 or SEQ ID NO: 11.

17. The production method according to claim 16, wherein the soluble thrombomodulin is a peptide consisting of a sequence consisting of amino acids at positions 19 to 516 of the amino acid sequence as set forth in SEQ ID NO: 9 or SEQ ID NO: 11, or a peptide that comprises a substitution, deletion, or addition of one or multiple amino acids in the amino acid sequence of said peptide and has thrombomodulin activity.

* * * * *